United States Patent [19]

Uehara et al.

[11] Patent Number: 5,034,888
[45] Date of Patent: Jul. 23, 1991

[54] ELECTRONIC ENDOSCOPE APPARATUS HAVING DIFFERENT IMAGE PROCESSING CHARACTERISTICS FOR A MOVING IMAGE AND A STILL IMAGE

[75] Inventors: Masao Uehara; Masahiko Sasaki; Akinobu Uchikubo; Katsuyuki Saito; Masahide Kanno, all of Tokyo, Japan

[73] Assignee: Olympus Optical Co., Ltd., Tokyo, Japan

[21] Appl. No.: 595,730

[22] Filed: Oct. 11, 1990

Related U.S. Application Data

[63] Continuation of Ser. No. 293,772, Jan. 5, 1989, abandoned.

[30] Foreign Application Priority Data

Feb. 26, 1988 [JP] Japan .................................. 63-44708
Nov. 1, 1988 [JP] Japan ................................ 63-277793

[51] Int. Cl.⁵ ........................ A61B 1/04; G02B 23/24; H04N 5/213
[52] U.S. Cl. ................................ 364/413.13; 358/98; 358/167
[58] Field of Search ................. 128/6; 358/98, 36, 37, 358/164, 166, 167; 364/413.13

[56] References Cited

U.S. PATENT DOCUMENTS

| 4,468,593 | 8/1984 | Fujita et al. | 358/78 |
| 4,699,125 | 10/1987 | Komatsu | 128/6 |
| 4,791,480 | 12/1988 | Muranaka | 358/98 |
| 4,805,016 | 2/1989 | Kato | 358/98 |
| 4,833,527 | 5/1989 | Kondo | 358/32 |
| 4,869,256 | 9/1989 | Kanno et al. | 128/6 X |
| 4,884,134 | 11/1989 | Tsuji et al. | 358/98 |
| 4,885,634 | 12/1989 | Yabe | 358/98 |

FOREIGN PATENT DOCUMENTS 61-94644  5/1986  Japan .
0152185  7/1986  Japan .
0228894  9/1988  Japan .

Primary Examiner—Clark A. Jablow
Attorney, Agent, or Firm—Armstrong, Nikaido, Marmelstein, Kubovcik & Murray

[57] ABSTRACT

An endoscope apparatus is arranged to convert the image signal output from an imaging device into a standard video signal, effect image processing, such as outline emphasis, of the image signal, and display a reproduced image on a display. The endoscope apparatus has the function of stopping input to a memory circuit in accordance with the on action of a freezing switch, switching from a moving image to a still image, and providing a display of the still image. Accordingly, it is possible to select appropriate image processing characteristics in accordance with whether a moving image or a still image is to be displayed.

20 Claims, 14 Drawing Sheets

134 VERTICAL OUTLINE EMPHASIS CIRCUIT

FREEZING SWITCH

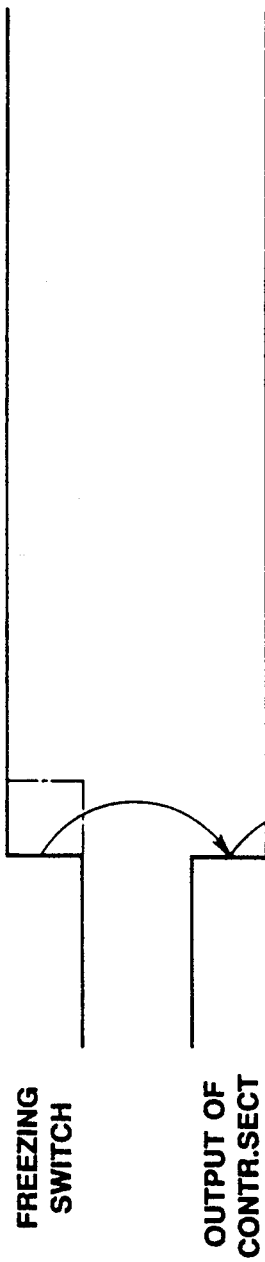
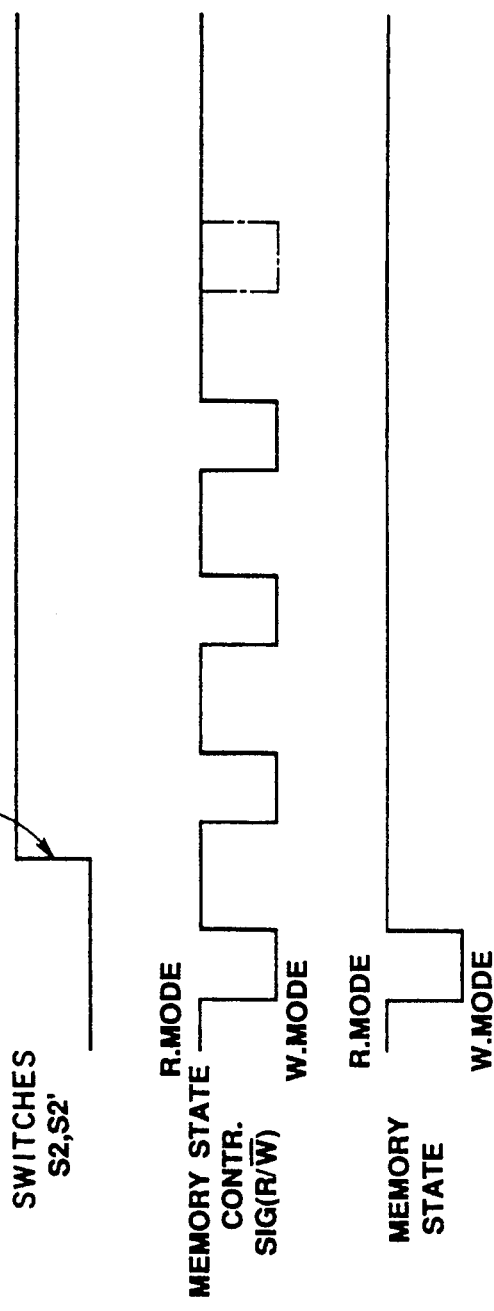
FIG.7a
FIG.7b
FIG.7c
FIG.7d
FIG.7e
FIG.7f

FIG.16
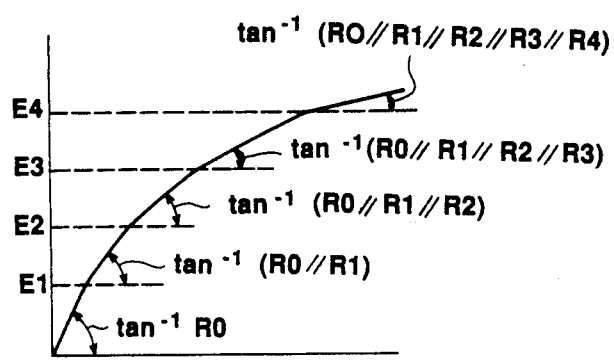
FIG.17a
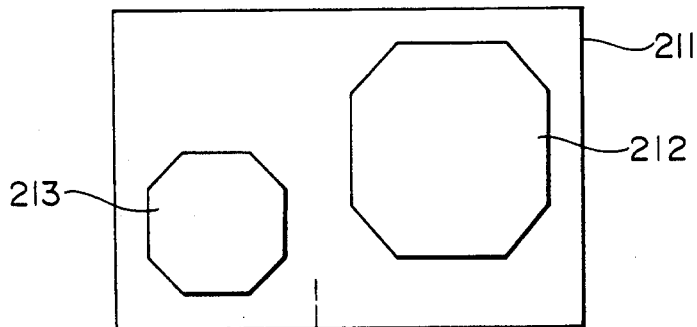
FIG.17b
FIG.17c
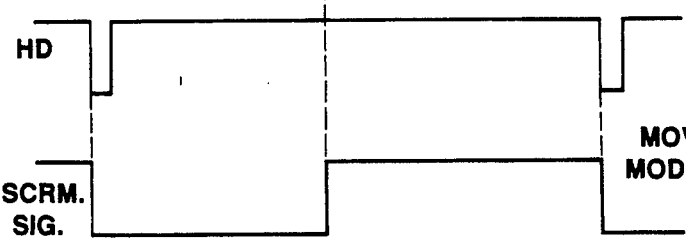

ELECTRONIC ENDOSCOPE APPARATUS HAVING DIFFERENT IMAGE PROCESSING CHARACTERISTICS FOR A MOVING IMAGE AND A STILL IMAGE

This is a continuation of application Ser. No. 293,772, filed Jan. 5, 1989, now abandoned.

BACKGROUND OF THE INVENTION

1. Field of the Invention

The present invention relates to an electronic endoscope apparatus which is capable of selecting different image processing conditions in accordance with whether a moving image or a still image is to be displayed.

2. Description of the Related Art

In recent years, solid state imaging devices such as charge-coupled devices (hereinafter referred to as the "CCD(s)") have been widely used as various kinds of imaging means. Television cameras, electronic endoscopes and so forth are known as such imaging means.

In Japanese Patent Laid-open No. 94644/1986, the present assignee proposes an electronic endoscope apparatus which is capable of independently varying the amount of outline emphasis of each color signal by means of an outline emphasis circuit, thereby enabling an improvement in the quality of an image.

FIG. 1 shows the construction of the aforementioned electronic endoscope apparatus.

The illustrated electronic endoscope apparatus according to the prior art comprises an (electronic) endoscope body 10, a video processor 12, an RGB/NTSC monitor 14, an NTSC monitor 16, an RF monitor 18, a recording/reproducing device 20, a light source unit 22 and a laser device 24. A solid state imaging device (for example, a CCD) 30 for imaging a body organ or a body cavity is provided at the distal end of the endoscope body 10. The output of the solid state imaging device 30 is supplied as a two-phase signal to the video processor 12 through a preamplifier 32. Further, a light guide 36 and a laser probe 38 are provided in the endoscope body 10. The laser probe 38 is inserted into, for example, a forceps channel and serves to introduce a laser beam from the laser device 24 into the distal end of the endoscope body 10, irradiating an object with the laser beam. The light guide 36 is constituted by an optical fiber bundle for introducing illuminating light from the light source unit 22 into the distal end, and serves to illuminate the body organ or the body cavity. Since the distal end of the endoscope body 10 is thin, the solid state imaging device 30 consists of a light receiving portion alone and does not have a light shielding-type storing portion which functions as a shutter. A shutter mechanism is provided in the light source unit 22 as will be described later.

An image signal which has been supplied from the preamplifier 32 to the video processor 12 is first input to a CMR amplifier 40. The output signal of the CMR amplifier 40 is passed through a sample and hold circuit 42, a low-pass filter 44, a band correcting circuit 46, an AGC circuit 48, a γ compensation circuit 50, an A/D converter 52 and a selector 54, in that order, and is supplied to a memory circuit 56. The low-pass filter 44 and the band correcting circuit 46 smooth the image signal. The memory circuit 56 is constituted by three frame memories 56-1, 56-2 and 56-3 for storing R, G and B images, respectively. The selector 54 has three output terminals which are connected to the R, G and B frame memories 56-1, 56-2 and 56-3, respectively.

The outputs of the memory circuit 56 are supplied to a 1H memory section 60 through a selector section 58. The 1H memory section 60 is divided into two parts for each color component. Each of the three R, G and B color components are written into the two parts of the corresponding 1H memory in an alternately switched manner every horizontal scanning period by the operation of the selector section 58. More specifically, the outputs of the frame memories 56-1, 56-2 and 56-3 are supplied to selectors 58-1, 58-2 and 58-3. Each of the selectors 58-1, 58-2 and 58-3 has two output terminals. The output of the selector 58-1 is connected to a 1H memory 60-1 or 60-2, the output of the selector 58-2 to a 1H memory 60-3 or 60-4, and the output of the selector 58-3 to a 1H memory 60-5 or 60-6. The output of the 1H memory 60-1 or 60-2 is connected to a D/A converter 64-1 through a selector 62-1, the output of the 1H memory 60-3 or 60-4 to a D/A converter 64-2 through a selector 62-2, and the output of the 1H memory 60-5 or 60-6 to a D/A converter 64-3 through a selector 62-3. The outputs of the D/A converters 64-1, 64-2 and 64-3 are supplied to band correcting circuits 68-1, 68-1 and 68-3 through low-pass filters 66-1, 66-2 and 66-3. The outputs of the band correcting circuits 68-1 and 68-3 are supplied to multipliers 70-1 and 70-3 and multiplied by white balance adjustment signals WB-1 and WB-3 so that the respective white balances are adjusted. The outputs of the multiplier 70-1, the band correcting circuit 68-2 and the multiplier 70-1 are supplied to the R, G and B input terminals of the RGB/NTSC monitor 14, respectively.

Simultaneously, the outputs of the multiplier 70-1, the band correcting circuit 68-2 and the multiplier 70-3 are supplied to an NTSC encoder 74. The output of the NTSC encoder 74 is supplied to both a first input terminal of a selector 76 and the input terminal of the recording/reproducing device 20. The reproduced signal of the recording/reproducing device 20 is supplied to a second input terminal of the selector 76 through a band correcting circuit 80. The NTSC signal output from the selector 76 is supplied through a switch 72 to the NTSC input terminal of the RGB/NTSC monitor 14, directly to the NTSC input terminal of the NTSC monitor 16, and to the RF monitor 18 through an RF modulator 78.

The output of the band correcting circuit 46 is supplied not only to the AGC circuit 48 but also to a voltage divider 85. The voltage divider 85 outputs a reference signal for each R, G and B image during automatic light control. The magnitude of the respective reference signals become small in the order of G, R and B. This is because the magnitudes of the color components of the respective G, R and B image signals become small in that order. Each voltage dividing point of the voltage divider 85 is connected to a corresponding input terminal of the selector 86, and the output signal of the selector 86 is supplied as an automatic light control signal to the light source unit 2 through a low-pass filter 88 and a comparator/amplifier 90.

The video processor 12 further includes an SID driver 91 for generating clock pulses used to drive the solid state imaging device 30. Each circuit in the video processor 14 is timing-controlled by a timing generator 82 or 84. The timing generator 82 receives the signal output from an operating switch 83 provided for controlling irradiation with a laser beam. The outputs of the timing generator 82 are supplied to the sample and hold circuit 42, the selector 54, the memory circuit 56, the selector 86 and the SID driver 91. The outputs of the timing generator 84 are supplied to the frame memory 56, the selector section 58, the 1H memory section 60, the selector section 62 and the NTSC encoder 74. The rate of writing to the memory circuit 56 differs from the rate of reading from the memory circuit 56, and writing to the memory circuit 56 is controlled by the timing generator 82 while reading from the memory circuit 56 is controlled by the timing generator 84. The sections 56 and 86 are controlled in synchronization with each other so that, for example, when either of them selects R, the other also selects R. The selector sections 58 and 62 are controlled so that they select mutually different 1H memories.

The light source unit 22 has a lamp 92 for emitting illuminating light to be incident upon the light guide 36. The illuminating light emitted from the lamp 92 is incident upon the light guide 36 through an iris plate 94, an optical system 96 and a rotary filter device 98. The iris plate 94 is constituted by a plate of predetermined thickness and having a plurality of through-holes. The iris plate 94 is rotated by a galvano motor 100 to change an angle with respect to the optical axis of the illuminating light, thereby adjusting the quantity of passing light by using the thickness of the through-holes. The galvano motor 100 is driven by automatic light control signals supplied from the comparator/amplifier 90. As described above, since the magnitude of the automatic light control signals of the respective image signals become smaller in the order of G, R and B, the amount of reduction becomes smaller in the order of G, R and B and, therefore, the levels of the color signals of the respective color components become uniform. The rotary filter device 98 has a shutter function and the function of coloring illuminating light in R, G and B. The rotary filter device 98 is constituted by a disk in which R, G and B color filters are non-continuously arranged around the circumference of a common circle. The non-continuous portions between adjacent color filters serve as a shutter for shielding light to be supplied to the solid state imaging device 30. Holes are formed outside the trailing edges of the respectively color filters in the direction of rotation of the rotary filter device 98, and a start pulse generating through-hole is formed outside the through-hole which is located outside the hole adjacent to the trailing edge of the R filter.

The rotary filter device 98 is rotated by a step motor 102. The step motor 102 rotates at a fixed speed under the control of a servo circuit 104. A light detector 106 is disposed in the vicinity of the edge of the rotary filter device 98. The light detector 106 consists of a light emitting diode and a light sensor, and receives the light passing through the through-hole, generating a read pulse and a start pulse.

The start pulse and read pulse output from the light detector 106 are supplied to the timing generator 82 in the video processor 12 through amplifiers 108 and 110, respectively.

The laser device 24 has a YAG laser 116 interposed between resonant mirrors 118-1 and 118-2, and the YAG laser 116 is excited by an excitation lamp 114 controlled by a lamp controlling circuit & electrical power source 112. The optical path between the YAG laser 116 and the resonant mirror 118-1 is selectively closed and opened by a shutter plate 120 connected to a solenoid 122. Thus, the laser beam of the YAG laser 116 is made incident upon the laser probe 38 in a pulsed manner. On-off action of the solenoid 122 is controlled by the timing generator 82 in the video processor 12.

In the electronic endoscope apparatus having the above-described arrangement, an image of the object which has been imaged by the solid state imaging device 30 is photoelectrically converted into an electrical signal, and the electrical signal is converted into an video signal in the sample and hold circuit 42. The video signal is outline-emphasized by the first band correcting circuit 46. Subsequently, the outline-emphasized signal is passed through the A/D converter 52, converted into synchronized R, G and B signals in the memory circuit section 56 for effecting synchronization of sequential signals. The R, G and B signals are converted into analog video signals in the respective D/A converters 64-1, 64-2 and 64-3 and supplied to corresponding second band correcting circuits 68-1, 68-2 and 68-3, in which the horizontal outline emphasis of the signals are effected.

Accordingly, the outline of the image of a portion to be diagnosed can be emphasized by these first and second band correcting circuits 46 and 68-1, 68-2 and 68-3, whereby the efficiency of diagnosis can be improved.

As will be readily conceived from the construction shown in FIG. 1, a frozen image can be obtained if the same data written in the memory section 56 is repetitively read out when the writing operation of the memory circuit 56 is stopped. In this case, the amount of emphasis of the outline of the frozen image (still image) equals that of emphasis of the outline of a real-time image, that is, a moving image.

In general, however, the resolution and noise of still images differ from those of moving images in terms of visual effects. Accordingly, the above-described example of the prior art still includes factors to be improved.

In such a situation, a reference is as known in which a noise reduction method for use in ultrasonic equipment had been proposed. Such a method, however, contemplates image processing of still images alone. Accordingly, it is impossible to realize real-time processing in terms of processing time and therefore to realize an improvement in the quality of real-time images (moving images) which are normally observed.

SUMMARY OF THE INVENTION

It is, therefore, an object of the present invention to provide an electronic endoscope apparatus which is capable of effecting image processing appropriate for each of a moving image and a still image.

It is another object of the present invention to provide an electronic endoscope apparatus which can provide an endoscopic image suitable for use in diagnosis.

To these ends, in accordance with the present invention, there is provided an electronic endoscope apparatus which comprises image-quality correcting device for effecting an appropriate amount of image correction in accordance with each of a moving image and a still image and a switching device for causing the image-quality correcting device to selectively effect image correction of each of a moving image and a still image.

With this arrangement, it is possible for an observer to obtain an image which is processed through visually optimum image correction whichever the observer may choose, a moving image or a still image. Accordingly, he can make a diagnosis, examination or the like even more accurately and rapidly.

BRIEF DESCRIPTION OF THE DRAWINGS

FIGS. 4a to 4h2 are waveform diagrams which serve to illustrate the operation of the vertical outline emphasis circuit of FIG. 2;

FIGS. 7a to 7f are waveform diagrams which serve to illustrate the operation of the first embodiment;

FIG. 16 is a characteristic chart showing the input-/output characteristics of the gamma compensation circuit shown in FIG. 15;

FIGS. 17a to 17c are views which serve to illustrate a fifth embodiment of the present invention;

DESCRIPTION OF THE PREFERRED EMBODIMENTS

The preferred embodiments of the present invention will be described below with reference to the accompanying drawings.

Figure 3:
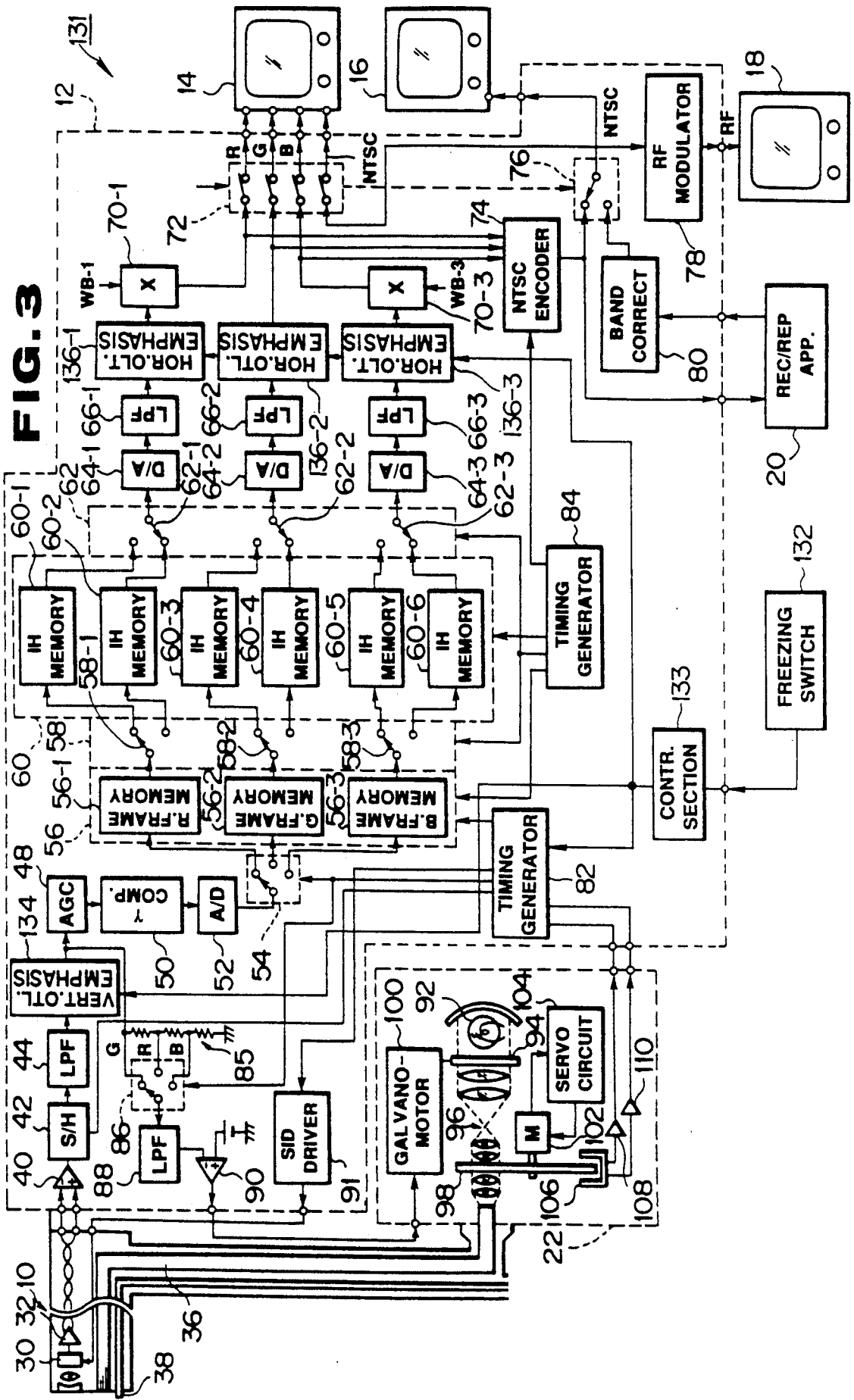
FIG. 3 is a block diagram showing an electronic endoscope apparatus according to the first embodiment.

FIG. 3 shows an electronic endoscope apparatus 131 according to a first embodiment of the present invention. The electronic endoscope apparatus 131 is an improved version of the electronic endoscope apparatus of FIG. 1 in that a freezing switch 132 is provided in place of the operating switch 83. The on/off signal output from the freezing switch 132 is input to a control section 133, and the control section 133 outputs a freeze-on control signal (corresponding to a still image) or a freeze-off control signal (corresponding to a moving image) in accordance with the operation of the freezing switch 132. More specifically, when the freezing switch 132 is switched on, the control section 133 controls, at that timing, a vertical outline emphasis circuit 134 to effect switching of the amount of correction thereof. An image signal is written into the memory circuit 56 in accordance with this switching. The output signal of the control section 133 is also input to the timing generator 82 and, when an image signal for one frame is written into the memory circuit 56, the timing generator 82 stops a write mode and thus the memory circuit 56 stops updating image data. The control section 133 is also arranged to control horizontal outline emphasis circuits 136-1, 136-2 and 136-3 to effect switching of the amount of correction thereof, the horizontal outline emphasis circuits 136-1, 136-2 and 136-3 being provided in place of the second band correcting circuits 68-1, 68-2 and 68-3 of FIG. 1, respectively.

Figure 2:
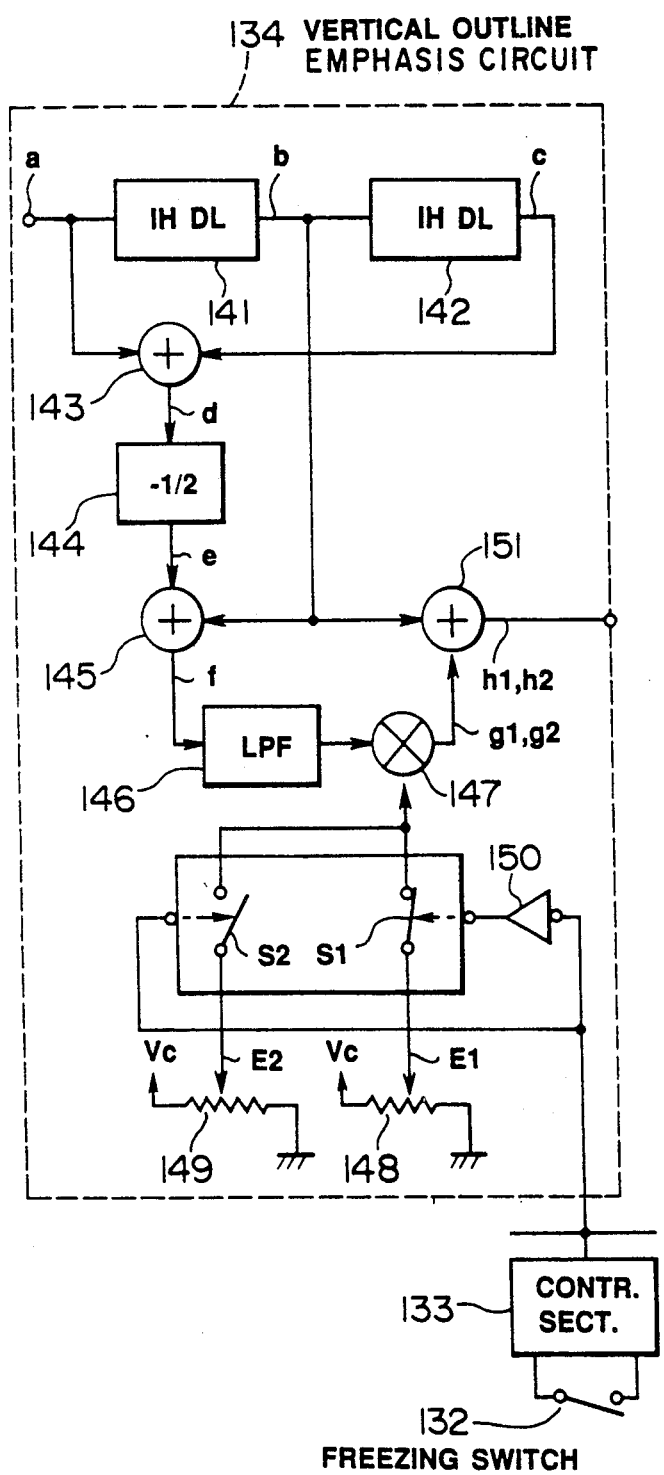
FIG. 2 is a block diagram showing a vertical outline emphasis circuit according to a first embodiment of the present invention.

FIG. 2 shows the construction of the vertical outline emphasis circuit 134 in the first embodiment.

The signal passed through the low-pass filter 44 is applied to the input terminal of the vertical outline emphasis circuit 134. The signal is delayed by one horizontal period (approximately 64 $\mu$sec) in a first 1H delay line 141 and then by another horizontal period in a second 1H delay line 142. Accordingly, if a signal such as that shown in FIG. 4a is applied to the input terminal, the signal passed through the delay line 141 is as shown in FIG. 4b and the signal passed through the delay line 142 is as shown in FIG. 4c.

The signal applied to the above input terminal and the signal delayed by the second delay line 142 are added in a first adder 143 and formed into the signal shown in FIG. 4d. The signal of FIG. 4d is applied to a x-½ multiplier 144, formed into the signal shown in FIG. 4e, and applied to a second multiplier 145. The adder 145 also receives the signal passed through the first 1H delay line 141 and adds these input signals to provide the signal shown in FIG. 4f. This signal is passed through a low-pass filter (LPF) 146 for passing low-band components and applied to an analog multiplier 147. This multiplier 147 is arranged to receive the set voltages E1 and E2 of variable resistors 148 and 149 through analog switches S1 and S2, respectively. The signal output from the control section 133 is applied to the control terminal of the analog switch S1 through an inverter 150, while the same signal is applied directly to the control terminal of the analog switch S2. In other words, the two analog switches S1 and S2 are selectively switched on in such a manner that when either of them is on, the other is off.

The variable resistor 148 serves to set the amount of correction of a moving image (the switch S1 is on when the freezing switch 132 is off), while the other variable resistor 149 serves to set the amount of correction of a still image. The voltage level at the variable terminal of the variable resistor 149 is selected to be closer to the voltage level at a power source terminal Vc than the voltage level at the variable terminal of the variable resistor 148, that is to say, the set voltages E2 and E1 are selected so that the relationship of E2>E1 is maintained.

When the analog switch S1 or S2 is switched on, the corresponding voltage E1 or E2 is applied to the multiplier 147, where it is added to the signal passed through the low-pass filter 146. If, for example, the switch S1 is switched on and a moving-image mode is selected, the output of the multiplier 147 assumes the waveform shown in FIG. 4$g1$. If the switch S2 is switched on and a still-image mode is selected, the output of the multiplier 147 assumes the waveform, shown in FIG. 4$g2$, having opposite edges whose amplitudes are greater than those of the opposite edges of the signal of FIG. 4$g1$. (This is because the set voltages E2 and E1 are selected so that the relationship of E2>E1 is maintained.)

Figure 4:
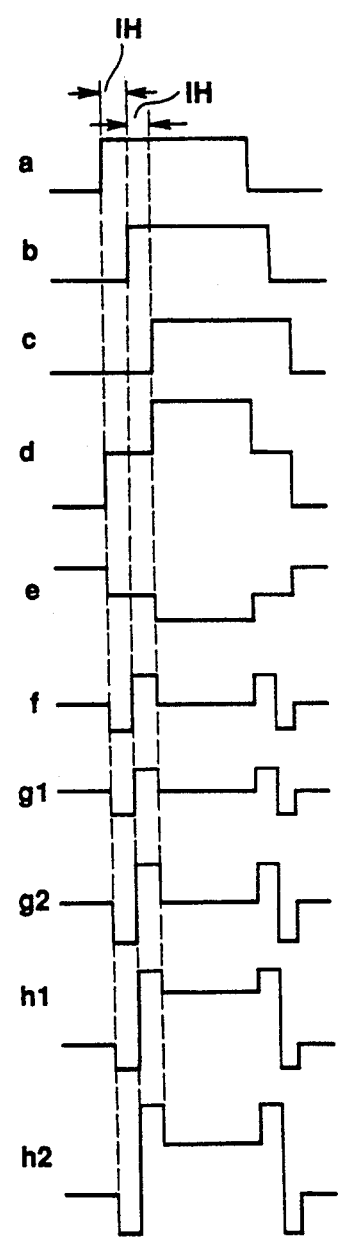

In an adder 151, the output signal g1 or g2 of the multiplier 147 are added to a signal b passed through the first 1H delay line 141. The adder 151 outputs a signal h1 or h2 whose vertical outline has been emphasized as shown in FIG. 4$h1$ or 4$h2$.

Figure 5:
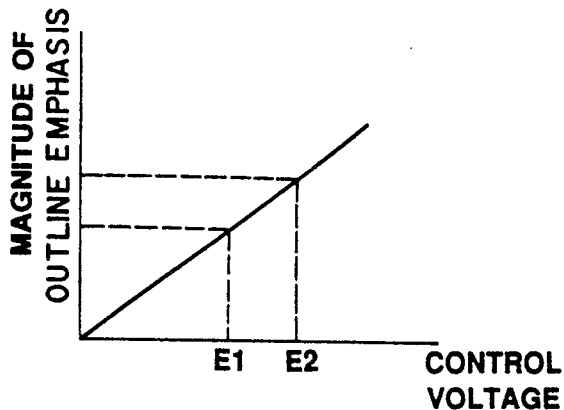
FIG. 5 is a characteristic chart illustrating that the amount of vertical outline emphasis varies in accordance with a control voltage.

FIG. 5 shows the relationship between the outline correction output from the multiplier 147 and the set voltages E1 and E2 of the respective variable resistors 148 and 149. As can be seen from FIG. 5, as the set voltage becomes higher, the multiplication coefficient becomes greater and hence the output correction output increases. In the first embodiment, the levels of the set voltages E1 and E2 are set at values which are suitable for use in processing a moving image and a still image, respectively.

Figure 6:
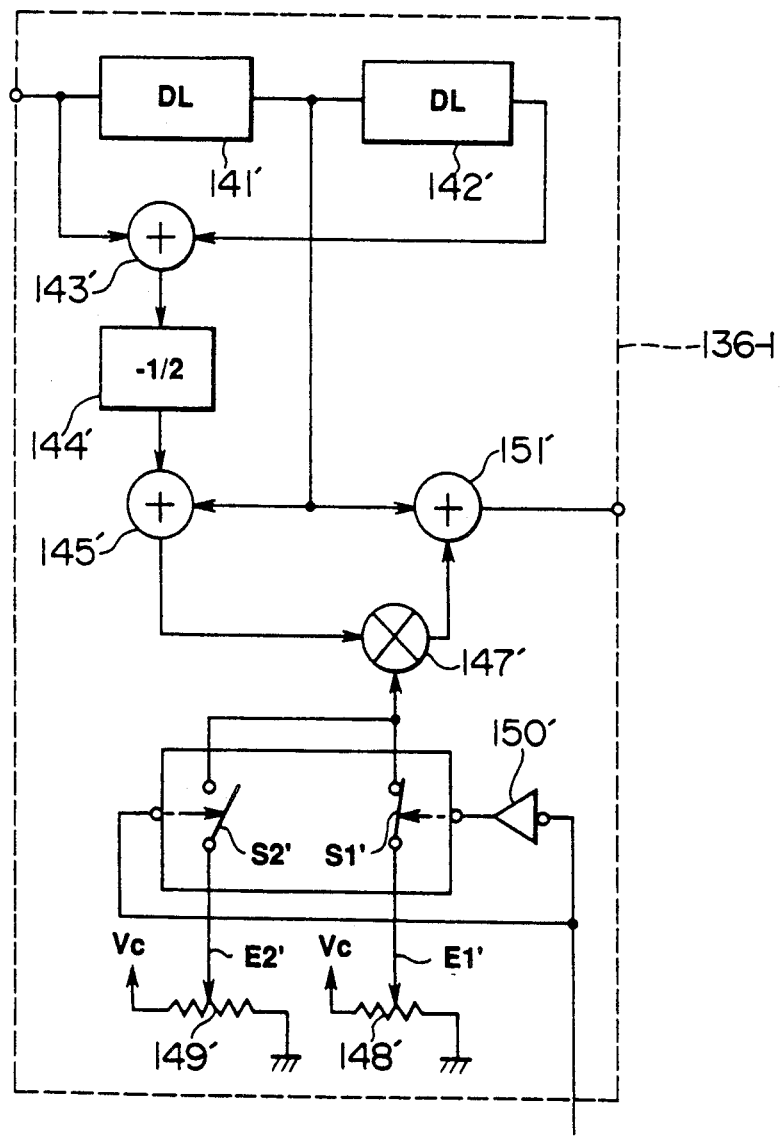
FIG. 6 is a block diagram showing a horizontal emphasis circuit according to the first embodiment.

The circuit constructions of the horizontal outline emphasis circuits 136-1 to 136-3 are the same as one another, and are shown in FIG. 6. The vertical outline emphasis circuit 134 shown in FIG. 2 is arranged to effect processing of the correlations between different lines, whereas each of the horizontal outline emphasis circuits 136-1 to 136-3 serves to effect outline emphasis of information signals contained in a single horizontal line whose period is much shorter than the period required for the processing of such line correlations. Accordingly, in each of the horizontal outline emphasis circuits 136-1 to 136-3, delay lines 141' and 142' which provide a delay of an even shorter period T (e.g. several hundred nsec) are employed in place of the 1H delay lines 141 and 142, respectively, and the low-pass filter 146 is not used. The delay lines 141' and 142' are capable of setting the amount of outline emphasis so that the amount of outline emphasis may reach its peak with respect to signal components of 2-2.5 MHz which remarkably influence an visual improvement in sharpness. The construction of the remaining portion of each of the horizontal outline emphasis circuits 136-1 to 136-3 is identical to that of the corresponding portion of the vertical outline emphasis circuit 134 and therefore "'" is affixed to each reference numeral in FIG. 6. In this case as well, variable resistors 148' and 149' serve to set the amounts of correction of a moving image and a still image, respectively, and the levels of set voltages E1' and E2' are set so that the relationship of E1'<E'2 is maintained.

Figure 1:
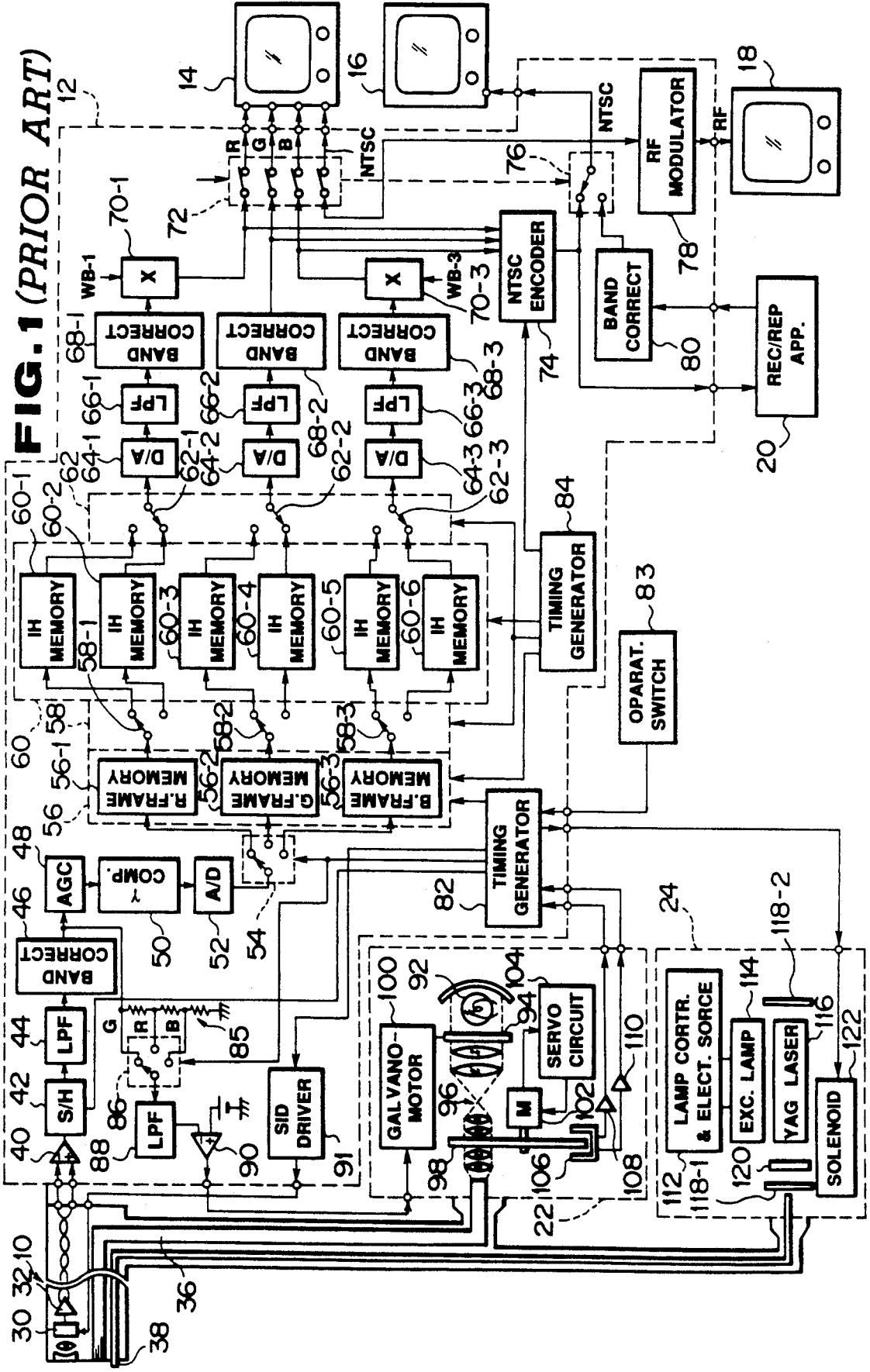
FIG. 1 is a block diagram showing an example of prior art.

The electronic endoscope apparatus 131 is not provided with the laser device 24 and its associated means both of which are shown in FIG. 1.

The construction of the remaining portions of the electronic endoscope apparatus 131 is substantially identical to that of the corresponding portions of the apparatus shown in FIG. 1, and therefore the same portions are denoted by the reference numerals which are the same as those used in FIG. 1.

In the above-described first embodiment, output light passed through the rotary filter device 98 illuminates an object in the form of R light, G light and B light in such a sequential manner as is shown in FIG. 7$a$. During each light shielding period, an image signal is read from the SID 30 in response to the drive signal output from the SID driver 91.

If the freezing switch 132 is off and a moving-image imaging mode is selected, a write mode is selected by a memory state control signal R/$\overline{W}$ output from the timing generator 82 and the signal which has been read from the SID 30 is written into the memory circuit 56. (The term "write mode" means a mode in which the signal read from the SID 30 is written into the memory circuit 56, and the data of the memory circuit 56 is read out even during the write mode.) In this state, the analog switches S1 and S1' are on, and the vertical outline emphasis circuit 134 and the horizontal outline emphasis circuits 136-1 to 136-3 emphasize the outline of a moving image by an appropriate amount. When the freezing switch 132 is switched on as shown in FIG. 7$b$, the output of the control section 133 goes to a low level as shown in FIG. 7$c$. In response to the output of the control section 133, the analog switches S2 and S2' of the respective outline emphasis circuits 134 and 136-1 to 136-3 are switched on (as shown in FIG. 7$d$) (, while the analog switch S1 and S1' are switched off.) As a result of this switching, the amount of outline emphasis of each of the outline emphasis circuits 134 and 136-1 to 136-3 is changed into an amount which is appropriate for the outline emphasis of a still image.

In the meantime, the output of the control section 133 is also input to the timing generator 82, and the timing generator 82 holds the memory circuit 56 in a read mode after R, G and B image signals have been stored in the memory circuit 56 by switching on the respective outline emphasis circuits 134 and 136-1 to 136-3. Accordingly, after the memory circuit 56 has stored image data whose vertical outline has been emphasized by an amount appropriate for the outline emphasis of a still image, the memory circuit 56 is held in a still image reproducing mode in which updating of data of the memory circuit 56 is stopped and hence identical image data is read out repetitively. In this case, since the horizontal outline emphasis circuits 136-1 to 136-3 effect horizontal outline emphasis by an amount appropriate for the emphasis of a still image, an observer can observe a still image having appropriate image quality.

If the freezing switch 132 is switched during a light shielding period as shown by one-dot chain line in FIG. 7$b$, that is, while the signal read from the SID 30 is being written to the memory circuit 56, the timing generator 82 holds the memory circuit 56 in a read mode after it has completed writing the SID signal for the next R field, that is, after it has completed the writing shown by one-dot chain line in FIG. 7$e$.

In the above-described first embodiment, since each of a still image and a moving image is outline-emphasized by an appropriate amount of correction, it is possible to obtain a still or moving image which is visually optimum. If either a moving image reproducing mode or a still image reproducing mode is selected in diagnosis using an endoscopic image, the observer can observe an image whose outline is emphasized by the amount of emphasis which is appropriate for the mode selected. Accordingly, the observer can easily make a diagnosis.

Although, in the above embodiment, the vertical outline emphasis circuit 134 is provided at the front side of the memory circuit 56, the circuit 134 may be provided at the rear side of the memory circuit 56 as will be described later. In the case of an arrangement in which the vertical outline emphasis circuit 134 is provided at the front side of the memory circuit 56, if the still image reproducing mode is selected, it is necessary to store in the memory circuit 56 signals which have been outline-emphasized by the amount of emphasis which is appropriate for the still image reproducing mode. For this reason, as shown in FIG. 7e, the amount of emphasis is switched over by operating the freezing switch 132 and an image signal for one color frame (in the case of R, G and B images, image signals for three frames) is stored in the memory circuit 56 and then writing to the memory circuit 56 is inhibited (updating of memory data is stopped).

On the other hand, if all the outline emphasis circuits are provided at the rear side of the memory circuit 56, it is possible to select an arbitrary amount of emphasis in accordance with the signals read from the memory circuit 56. In this case, therefore, as shown in not FIG. 7e but FIG. 7f, when the freezing switch 132 is switched on, the memory circuit 56 is immediately switched from the write mode to the read mode. On the other hand, if the freezing switch 132 is switched on during writing, the memory circuit 56 may be switched from the write mode to the read mode at the same time or after the relevant writing has been completed. If the switching of the mode of the memory circuit 56 is effected simultaneously with the switching of the freezing switch 132, the amount of outline emphasis is only changed at an intermediate time during the period required to display an image for one color frame and the subsequent image is outline-emphasized by a desirable mount.

If all the outline emphasis circuits are provided at the front side of the memory circuit 56, control may be provided as shown in FIG. 7e.

In the first embodiment described above, when the freezing switch 132 is switched on, the control section 133 outputs a switching signal to the outline emphasis circuits 134, 136-1, 136-2 and 163-3 so as to effect switching of each of them and, at the same time, a signal to the timing generator 82 so as to cause it to control the switching between the read and write modes as shown in FIG. 7e.

Figure 8:
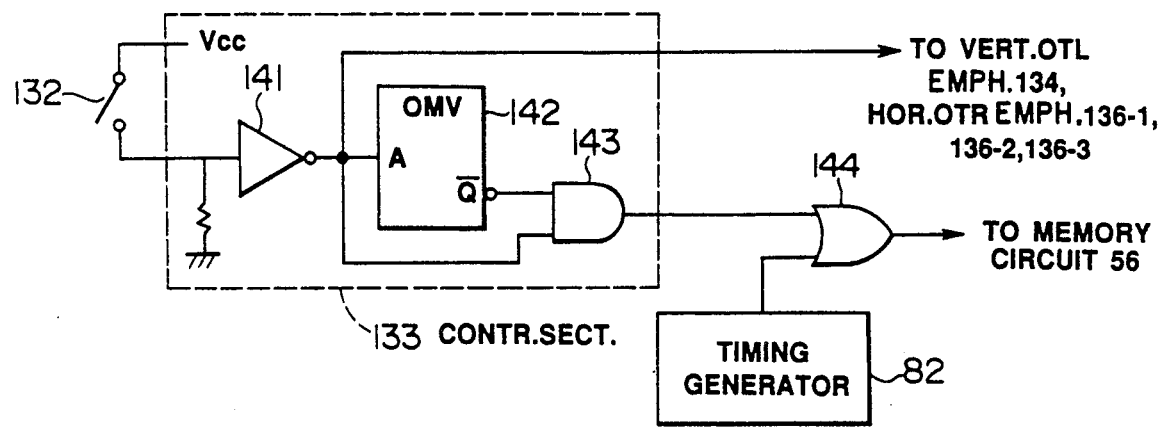
FIG. 8 is a block diagram showing the construction of a control section usable in the first embodiment.

The control section 133 itself can provide control over the outline emphasis circuits 134, 136-1, 136-2 and 136-3 as well as the timing generator 82. FIG. 8 shows the construction of the circuit required to achieve such control.

As illustrated, the on/off signal issued by the freezing switch 133 is inverted by an inverter 141 and applied to each of the outline emphasis circuits 134, 136-1, 136-2 and 136-3 as a switching signal. The signal thus inverted is input to a one-shot multivibrator (abbreviated as the "OMV") 142. The OMV 142 is started by the rising edge of the inverted signal to output a signal of pulse width corresponding to one color frame period. The inverted output $\overline{Q}$ of the OMV 142, together with the output of the inverter 141, is input to an AND circuit 143, and the AND circuit 143 outputs a signal which goes to a high level with a delay of one color frame period after the switch 133 has been switched on. In response to this signal, an OR circuit 144 controls switching of the read/write switching signal R/$\overline{W}$ applied from the timing generator 82 to the memory circuit 56. (A delay device may be employed in place of the OMV 142 and the AND circuit 143.)

In other words, when the freezing switch 133 is switched on, the AND gate 143 outputs a signal which goes to a high level one frame period after the timing shown in FIG. 7d. Accordingly, the output signal of the timing generator 82 which has been passed through the OR circuit 144 assumes the waveform shown in FIG. 7f.

FIG. 9 shows a modified example of the first embodiment of the present invention which employs a horizontal outline emphasis circuit 161 and a vertical outline emphasis circuit 162.

The above output circuits 161 and 162 may be provided at the front or rear side of the memory circuit 56. If they are provided at the front side, writing to the memory circuit 56 may be inhibited, as described above, after a color image signal for one frame has been written into the memory circuit 56 by switching on the freezing switch 132. As a matter of course, if the output circuits 161 and 162 are provided at the rear side of the memory circuit 56, control may be provided in accordance with the control procedures used when they are provided at the front side.

Figure 9A:
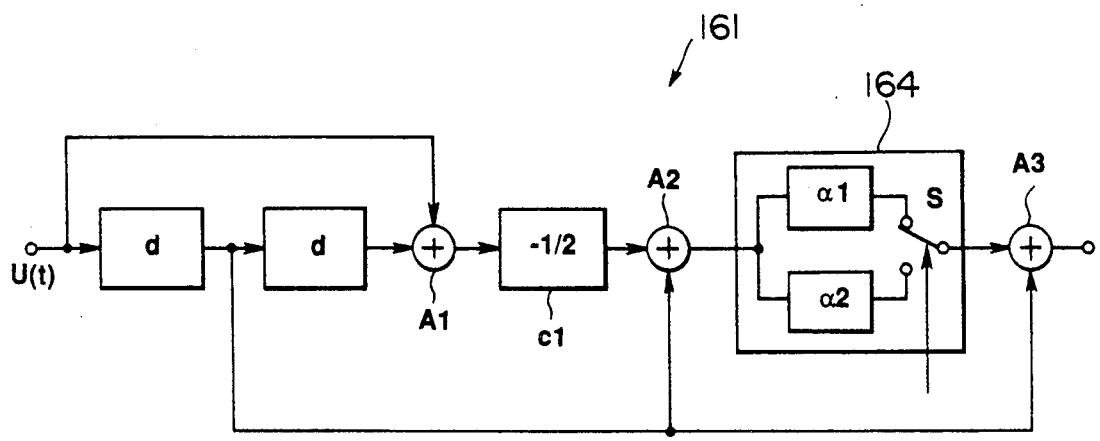
FIGS. 9a and 9b are block diagrams respectively showing a horizontal outline emphasis circuit and a vertical outline emphasis circuit which are used in a modified example of the first embodiment.

In the circuit construction shown in FIG. 9a, an input video signal U(t) is outline-emphasized in the horizontal direction by a combination of two delay elements d (each having the amount of delay equivalent to, for example, 200-250 nsec), adders A1, A2 and A3, a x-½ multiplier cl, and a multiplier 164 which can be switched between coefficients $\alpha 1$ and $\alpha 2$.

The multiplier 164 has a switch S which can be switched between the coefficients $\alpha 1$ or $\alpha 2$ in response to a control signal. The coefficients $\alpha 1$ and $\alpha 2$ are set at values which are appropriate for the emphasis of a moving image and a still image, respectively. Circuits for generating the coefficients $\alpha 1$ and $\alpha 2$ may be constituted by, for example, amplifiers.

Figure 9B:
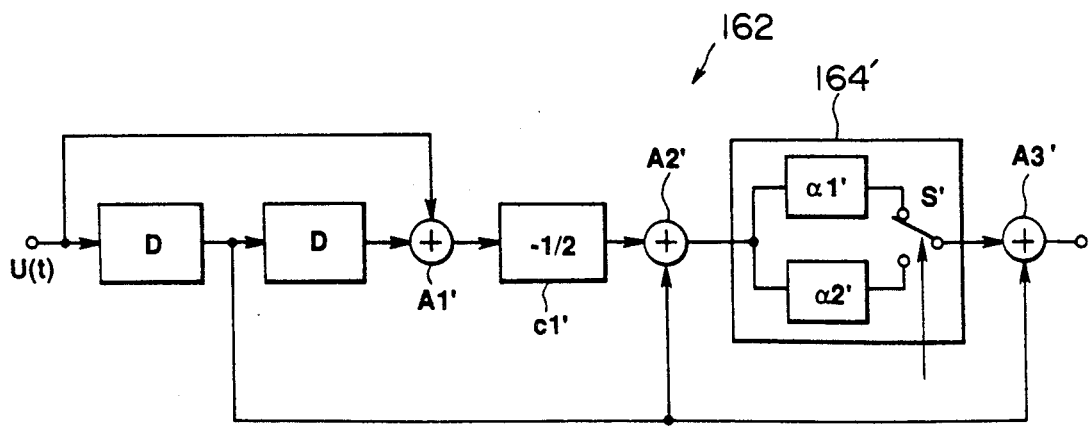

The circuit arrangement shown in FIG. 9b employs 1H delay elements D in place of the delay elements d described above. The construction of the remaining portion of the circuit arrangement of FIG. 9b is substantially identical to that of the corresponding portion of the one shown in FIG. 9a and therefore "'" is affixed to each reference numeral in FIG. 9b.

The circuit arrangements shown in FIGS. 9a and 9b are substantially identical to the circuit arrangements shown in FIG. 2 and 6. Although vertical outline emphasis and horizontal outline emphasis are separately effected in the above-described embodiment, vertical outline emphasis and horizontal outline emphasis may be simultaneously effected using an outline emphasis circuit such as that shown in each of FIGS. 10a to 10c. In this case, in the apparatus shown in, for example, FIG. 3, such a circuit may be provided in place of the horizontal outline emphasis circuits 136-1 to 136-3 and the vertical outline emphasis circuit 134 may not be provided at the front side of the memory circuit 56.

Figure 10:
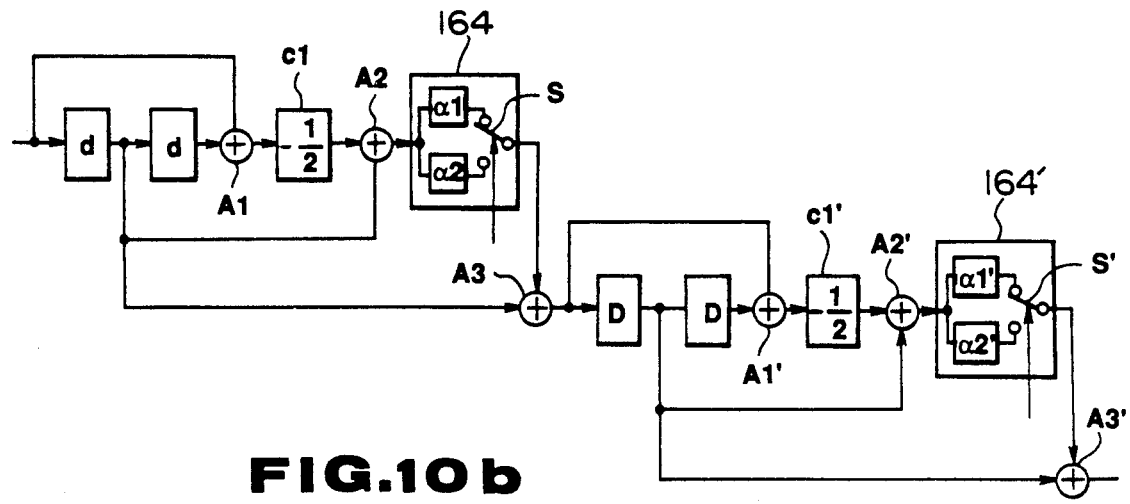
FIGS. 10a, 10b and 10c are block diagrams respectively showing outline emphasis circuits usable in the first embodiment.
Figure 10:
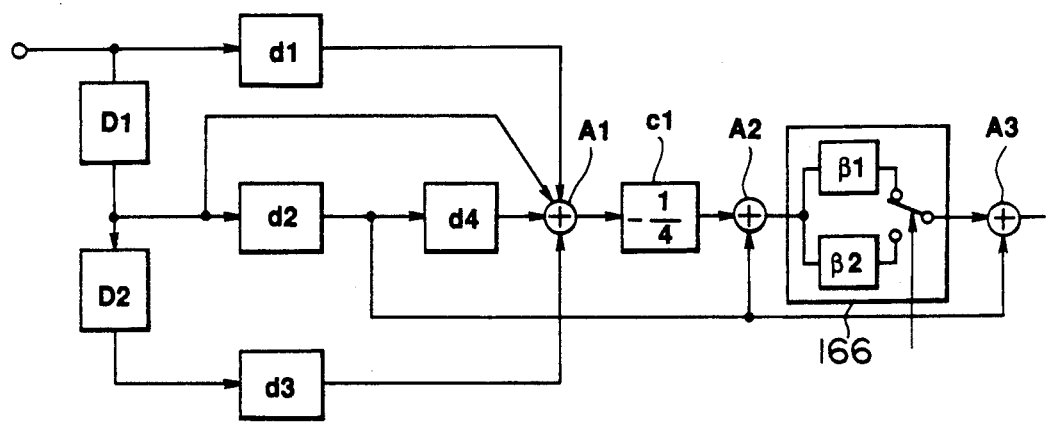
Figure 10:
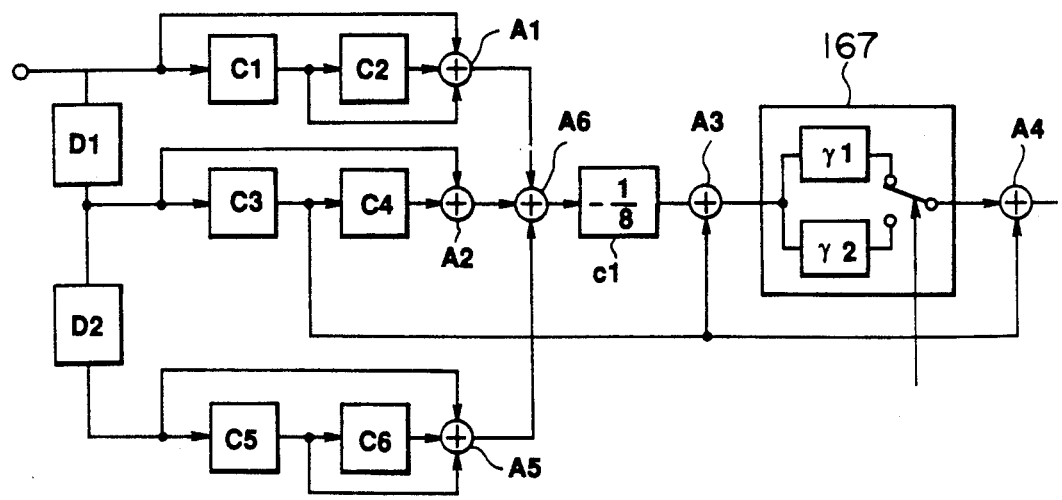

FIG. 10a shows a circuit construction composed of a serial connection of those shown in FIGS. 9a and 9b. Therefore, the elements shown in FIG. 10a are denoted by the reference numerals which are the same as those used in FIGS. 9a and 9b.

In the circuit construction shown in FIG. 10b, one part of an input signal is input to the adder A1 through the delay element dl having a delay of, for example, 200-250 ns, while the other part is input to the delay element having a delay of one horizontal period. The signal passed through the delay element D1 is input to the adder A1, the delay element d2 and the delay element D2. The signal passed through the delay element D2 having a delay of one horizontal period is input to the adder A1 through the delay element d3. One part of the signal passed through the delay element d2 is input to the adders A2 and A3, while the other part is input to the adder A1 through the delay element d4. The signal obtained by addition in the adder A1 is passed through a x-¼ multiplier cl and supplied to the adder A2, where it is added to the signal passed through the delay element d2. The resultant signal is passed through a multiplier 166, multiplied by $\beta1$ or $\beta2$, and added to the signal from the delay element d2 in the adder A3. Thus, the adder A3 outputs a signal which is outline-emphasized in the horizontal and vertical directions. The delay elements Di (i=1, 2, 3 and 4) have a delay of 200-250 nsec.

The switching between the coefficients $\beta1$ and $\beta2$ can be effected by the analog switch S in accordance with the operation of the freezing switch. The coefficients $\beta1$ and $\beta2$ are set in advance at values which are appropriate for the outline emphasis of a moving image and a still image, respectively.

FIG. 10c shows a multiple outline emphasis circuit capable of effecting outline emphasis in any of the vertical, horizontal and oblique directions while taking account of the peripheral factor of each pixel.

In the circuit construction shown in FIG. 10c, one part of an input signal is input to the adder A1, while the other part is input to the adder A1 through the delay element C1 having a delay equivalent to one pixel. The signal passed through the delay element C1 is passed through a delay element C2 and supplied to the adder A1, wherein it is added to the above-described signals.

A part of the input signal which has passed through the delay element D1 having a delay of one horizontal period is input to both the adder A2 and the delay element D2.

The other part of the signal passed through the delay element D1 is applied to a delay element C3. One part of the signal passed through the delay element C3 is input to the adder A3 as well as an adder A4, while the other part is input to the adder A2 through a delay element C4, where it is added to the signal from the delay element D1. One part of the signal passed through the delay element D2 is input to an adder A5, while the other part is input to a delay element C5. One part of the signal passed through the delay element c5 is directly input to the adder A5, while the other part is input to the adder A4 through the delay element C6. These three signals are added in the adder A5. The signals obtained by addition in the respective adder A1, A2 and A5 are added in the following adder 6. The result of the addition is passed through a x-⅜ multiplier cl, added to the signal from the delay element C3, and input to a multiplier 167, where the signal is multiplied by a coefficient $\gamma1$ or $\gamma2$. The result is added to the signal from the delay element C3 in the adder A4, and thus the adder A4 outputs a signal whose outline is emphasized in multiple directions.

Figure 11:
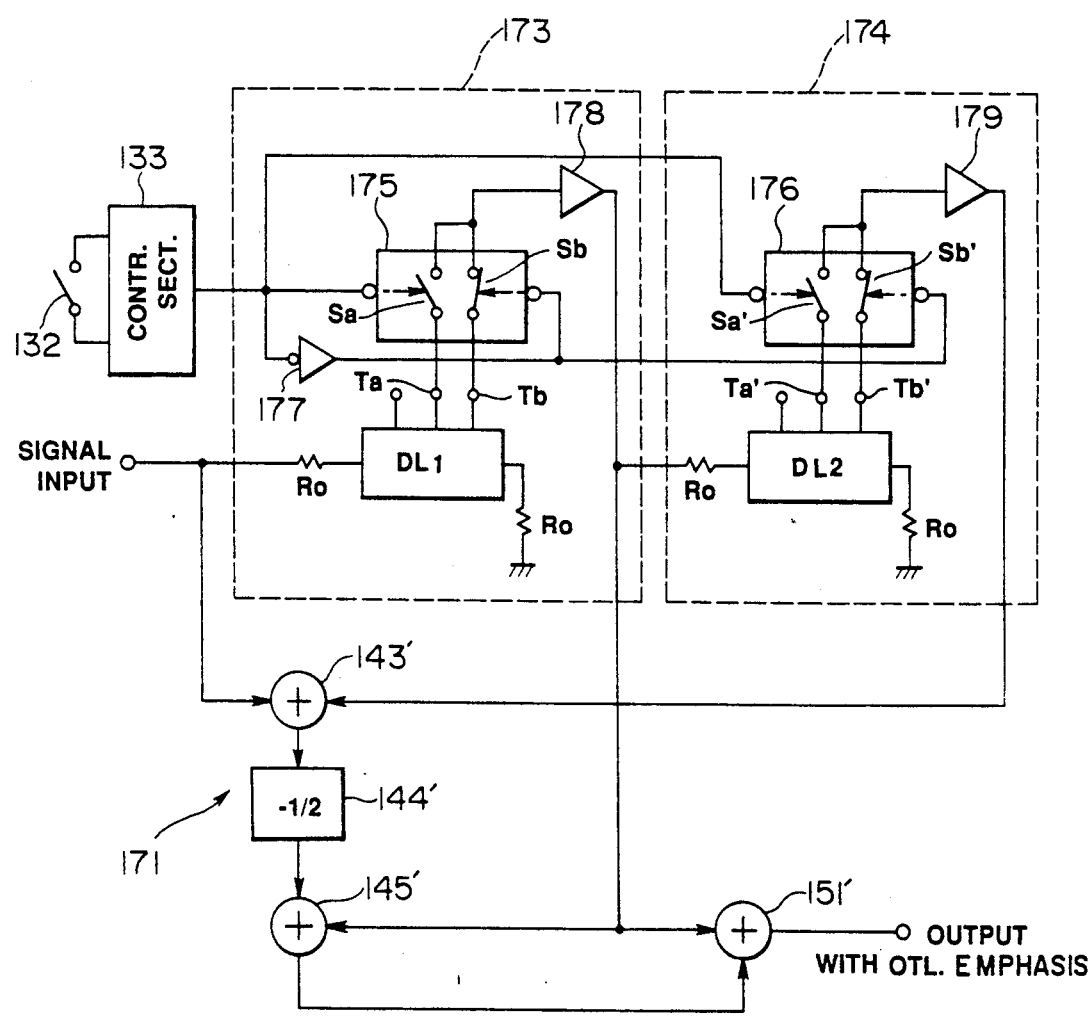
FIG. 11 is a block diagram showing a horizontal outline emphasis circuit according to a second embodiment.
Figure 12:
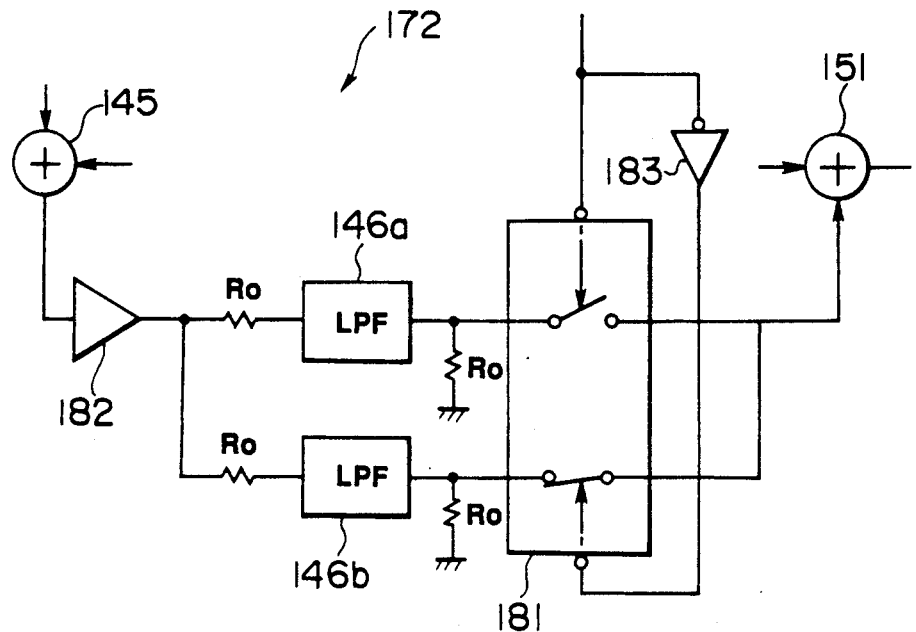
FIG. 12 is a block diagram showing a portion of a vertical outline emphasis circuit according to the second embodiment.

FIG. 11 shows a horizontal outline emphasis circuit 117 according to a second embodiment of the present invention, with FIG. 12 showing a vertical outline emphasis circuit 172 according to the second embodiment.

The horizontal outline emphasis circuit 171 shown in FIG. 11 is an improved version of the circuit shown in FIG. 6 in that the adder 147' is omitted from the input line through which the output of the adder 145' is input to the adder 151' and in that the delay lines 141' and 142' are respectively replaced with tapped delay lines DL1 and DL2 each having a different amount of delay, to form delay circuits 173 and 174 for effecting switching of the amount of delay in accordance with whether a moving image or a still image is to be processed, thereby changing the band of emphasis frequencies.

In the circuit construction shown in FIG. 11, the switch-on or switch-off signal generated by the freezing switch 132 is input to the control section 133. When the freezing switch 132 is off, the control section 133 outputs a high-level signal, while when the freezing switch 132 is on, the control section 133 outputs a low-level signal. Two analog switches 175 and 176 have mutually similar circuit constructions, including switches Sa and Sb and switches Sa' and Sb', respectively. The output of the control section 133 provides on-off control over the switches Sa and Sa' and, through the inverter 177, the switches Sb and Sb'. The switches Sa and Sa' are connected to the taps Ta and Ta' of the delay lines DL1 and DL2, respectively, these taps having a small amount of delay, while the other switches Sb and Sb' are connected to taps Tb and Tb' having a large amount of delay, respectively. The switches Sa to Sb' may be, for example, of a type which is switched on in response to a low-level signal. In this case, as shown in FIG. 11, when the freezing switch 132 is switched off, the switches Sb and Sb' are switched on. The outputs of the analog switches 175 and 176 which have passed through the corresponding delay lines DL1 and DL2 are output through buffers 178 and 179, respectively. As illustrated, matching resistors Ro are connected to the input and output terminals of each of the delay lines DL1 and DL2.

In the illustrated horizontal outline emphasis circuit 171, the amount of delay is switched over by switching on and off the freezing switch 132. More specifically, the amount of delay may be increased for the case of emphasis of a moving image, whereas, for the case of emphasis of a still image, the amount of delay may be decreased to switch the emphasis frequency from a lower frequency to a higher frequency.

The vertical outline emphasis circuit 172 shown in FIG. 12 is an modified version of the vertical outline emphasis circuit 134 shown in FIG. 2 in that an analog switch 181 is provided in place of the multiplier 147 so as to switch two low-pass filters 146a and 146b to each other.

The signal passed through the adder 145 is input to a buffer 182, and the output of the buffer 182 is input to the low-pass filters 146a and 146b through corresponding matching resistors Ro. The outputs of the respective low-pass filters 146a and 146b are input to an adder 151 through the analog switch 181.

The higher cutoff frequencies of the respective low-pass filters 146a and 146b are set to mutually different values; for example, the high-band cutoff frequency of the low-pass filter 146a is selected to be higher than that of the low-pass filter 146b. In other words, the transmission bandwidth of the circuit which includes the low-pass filter 146a to process a still image is selected to be wider than that of the circuit which includes the low-pass filter 146b to process a moving image. The analog switch 181 is arranged such that, in response to the output signal of the control section 133 (refer to FIG. 9), the element corresponding to the low-pass filter 146b is switched on in the case of a moving image, while, in the case of a still image, the element corresponding to the low-pass filter 146s is switched on. The output terminals of the low-pass filters 146a and 146b are grounded through the matching resistors Ro, respectively.

Figure 13:
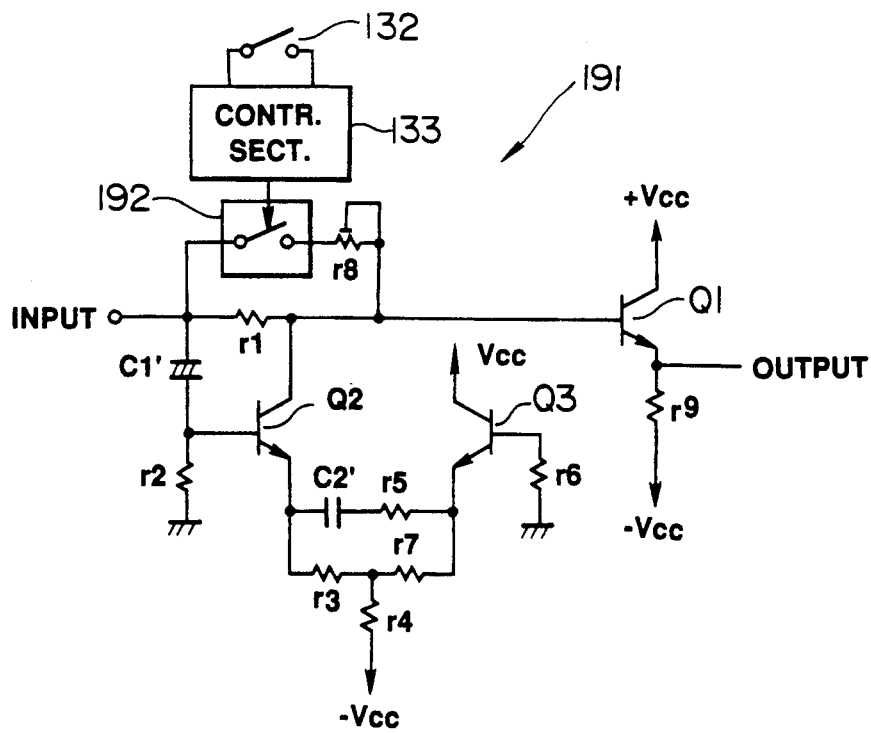
FIG. 13 is a circuit diagram showing a core-ring circuit according to a third embodiment.

FIG. 13 shows a core-ring circuit 191 according to a third embodiment of the present invention. The core-ring circuit 191 has the function of suppressing a low-level portion of an input signal to make noise nonconspicuous.

A part of an input signal is input to an emitter follower type transistor Q1 through a resistor r1, while the remaining part is input to the base of a transistor Q2 through a capacitor C1'. The base of the transistor Q2 is grounded through a resistor r2, while the emitter of the transistor Q2 is connected to a negative power source terminal −Vcc through resistors r3 and r4 as well as the emitter of a transistor Q3 through a capacitor C2 and a resistor r5. The base of the transistor Q3 is grounded through a resistor r6, its collector is connected to a positive power source terminal +Vcc, and its emitter is connected to the connection point between the resistors r3 and r4 through a resistor r7. The collector of the transistor Q2 is connected to the base of the transistor Q1 and to an input terminal through a variable resistor r8 and an analog switch 192. The emitter of the transistor Q1 is connected to the negative power source terminal −Vcc through the resistor r9, while the collector of the same is connected to the positive power source terminal +Vcc.

When the freezing switch 132 is switched on, the analog switch 192 is switched off under the control of the control section 133, and the combined resistor changes from r1//r8 to r1. (In this case, r1//r8 represents the combined resistance of the resistors r1 and r8 which are connected in parallel.)

The illustrated core-ring circuit 191 is arranged so that the value of a current flowing when the transistor Q2 is switched on is varied in accordance with whether the resistor r1 or the combined resistance or resistor r1//r8 is selected at the time of signal input to thereby vary the potential of a signal applied to the base of the transistor Q1 in accordance with the value of such a current. Accordingly, as shown in FIG. 14, if the input level of a portion of a signal is small, the output level of the portion is suppressed, that is to say, an input signal containing noise is output with the noise suppressed.

Figure 14:
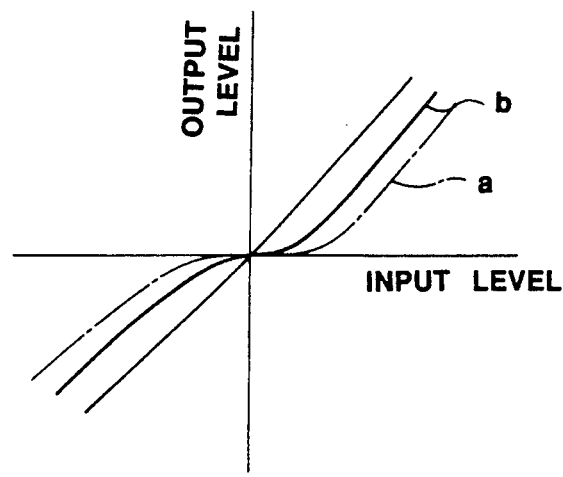
FIG. 14 is a characteristic chart showing the input-/output characteristics of the core-ring shown in FIG. 13.

In FIG. 14, a curve b corresponds to a moving image and is basically formed using the resistors r1//r8 and r4, while a curve a corresponds to a still image and is formed using the resistors r1 and r4.

If the core-ring circuit 191 is provided, for example, at the rear side of the horizontal outline emphasis circuits 136-1 to 136-3 shown in FIG. 3, it is possible to suppress noise which is conspicuous particularly when a still image is reproduced.

In general, when the noise of a moving image is compared with that of a still image, the visual form of noise in the former differs from that of noise in the latter, that is, the influence of noise upon the moving image differs from that of noise upon the still image. For example, in the case of the moving image, noise is not fixed and gives a kind of sandy sensation, but, in the case of the still image, noise is observed in a fixed state. However, the above-described core-ring circuit 191 can serve to select input/output characteristics which match either a still image or a moving image, thereby enabling noise to be suppressed to a nonconspicuous level. Accordingly, it is possible to provide a high-quality image.

Figure 15:
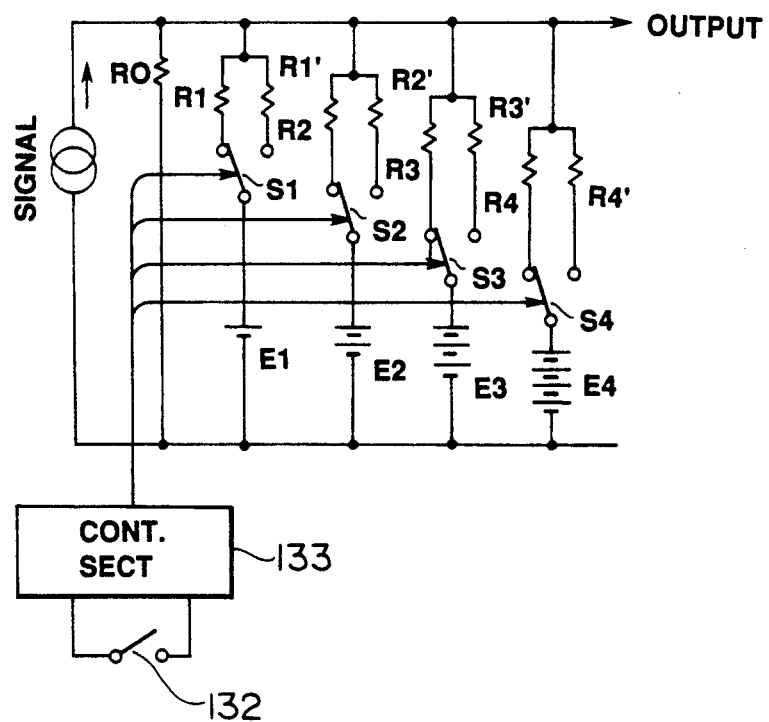
FIG. 15 is a circuit diagram showing the construction of a gamma compensation circuit according to a fourth embodiment.

FIG. 15 shows a gamma compensation circuit 201 according to a fourth embodiment of the present invention.

The gamma compensation circuit 201 is provided in place of, for example, the γ compensation circuit 50 shown in FIG. 3.

In the gamma compensation circuit 201, the following elements are connected to an input terminal to which a signal is input: a resistor R0; a series circuit which is formed between an electrical power source E1 and a resistor R1 or R1' by a switch S1; a series circuit which is formed between an electrical power source E2 and a resistor R2 or R2' by a switch S2; a series circuit which is formed between an electrical power source E3 and a resistor R3 or R3' by a switch S3; and a series circuit which is formed between an electrical power source E4 and a resistor R4 or R4' by a switch S4. Switching of each of the switches S1 to S4 is controlled by the control section 133 in accordance with the on-off action of the freezing switch 132. For example, in the case of a moving image, the resistors R1 to R4 shown in FIG. 15 are selected and the resultant γ characteristic becomes an input/output characteristic such as that shown in FIG. 16. When the freezing switch 132 is switched on, the switches S1 to S4 are switched to select the resistors R1' to R4'. Accordingly, a γ characteristic which differs from that shown in FIG. 16 is obtained.

The values of the respective resistors R1 to R4 are set to values which are appropriate for processing of a moving image, while the values of the respective resistors R1' to R4' are set to values which are appropriate for processing of a still image.

It is, therefore, possible to adjust the contrast of an image by changing the γ characteristic in accordance with whether a moving image or a still image should be reproduced. In general, a still image is often used when diagnosis which is stricter than that obtained by examining a real-time image used for ordinary observation is needed. In this case, if an image whose contrast is appropriated adjusted can be observed (e.g. on an enlarged scale), an operator will be able to make diagnosis by, for example, enlarging a subtle difference in contrast between the unaffected portion and the affected portion.

Although the gamma compensation circuit 201 is arranged to switch the g characteristics from one to another by effecting switching between the resistors R1 to R4 and the resistors R1' to R4', the arrangement of the gamma compensation circuit 201 is not limited to the above-described one. For example, the gamma compensation circuit 201 may be arranged to select from among a plurality of γ characteristics at the time of freezing.

Although the gamma compensation circuit 201 shown in FIG. 15 is arranged to effect switching between the resistors R1 to R4 and the resistors R1' to R4', two gamma compensation circuits each having a different γ characteristic may be provided so that they may be switched therebetween in accordance with whether a moving image or a still image is to be processed.

FIGS. 17a to 17c are views which serve to illustrate an image displayed on a monitor according to a fifth embodiment of the present invention.

The fifth embodiment is arranged so that a parent screen 212 and a child screen 213 are displayed on the display screen of a monitor 211.

When an even stricter diagnosis is needed in the diagnosis of an organ in the body cavity, a still image is often utilized. In this case, however, since a moving image of an area near the front end of an endoscope cannot be obtained, a dangerous accident may take place. To solve this problem, an electronic endoscope apparatus according to the fifth embodiment includes a so-called TV-in-TV function (parent-child television) of the type which is used in a general television receiver, and has the function of displaying a still image on the parent screen 212 and a moving image on the child screen 213. In addition, in this embodiment, the parent screen 212 and the child screen 213 are displayed in a horizontally spaced apart relationship and the boundary between the parent screen 212 and the child screen 213 is detected so that each of the above-described embodiments may be applied to the parent screen 212 and the child screen 213.

A horizontal synchronizing signal HD such as that shown in FIG. 17b is used as the trigger input signal of, for example, a monostable multivibrator (abbreviated as the "MSMV") to cause the MSMV to output a discriminating signal (FIG. 17c). The discriminating signal is held at a low level while the child screen 213 is being scanned, that is, until the horizontal scanning reaches the boundary between the child screen 213 and the parent screen 212. When the horizontal scanning has entered that boundary, the discriminating signal goes to a high level and is subsequently maintained at the high level. Such an output is used as a control signal (in place of the control signal of the control section 133) to effect switching of the outline emphasis circuit described above. When the output is at a low level, outline emphasis having a characteristic which matches a moving image is selected, while, when the output is at a high level, outline emphasis having a characteristic which matches a still image is selected.

Furthermore, a clock whose frequency is higher than that of the horizontal synchronizing signal, for example, a subcarrier (3.579545 MHz in the NTSC system) is input to a counter. In this case, the counter is reset by the horizontal synchronizing signal, and all the frequency-divided outputs are reset to a low level. The outputs of frequency division terminals go from the low level to a high level at the boundary between the child screen 213 and the parent screen 212 on the basis of the subsequent counting. Such an output is used as the discriminating signal shown in FIG. 17c. (As occasion demands, a plurality of outputs and gates may be combined to maintain the level of the output at the high level during scanning of the parent screen 212). The thus-obtained discriminating signal is used to effect switching of the analog switches used in each of the above-described embodiments.

In the field of processing of endoscopic images, the present assignee files several applications for patents concerning a so-called color enhancement circuit which is capable of enhancing the saturation and hue of a particular color of a blood vessel, the affected portion and so forth to improve the efficiency and accuracy of diagnosis. (Japanese Patent Laid-open No.13091/1987, Japanese Patent Application No.259512/1986, Japanese Patent Application No.296235/1986, Japanese Utility Model Laid-open No.202508/1986, Japanese Patent Application No. 69912/1987, Japanese Patent Application No.283566/1986, Japanese Patent Application No.302155/1986 and Japanese Patent Application No. 202730/1987).

The present invention can be applied to the color enhancement circuits disclosed in the above patent applications.

In each of the above-described embodiments, the image-quality determination factors incorporated in the outline emphasis circuit can be automatically switched over in association with the operation of the freezing switch. However, an arrangement in which these factors are manually switched over may be adopted. In addition, an arrangement in which manual switching and automatic switching can be selectively used may also be adopted.

Further, the range of application of the prevent invention is not limited only to a frame-sequential type of color imaging system. For example, the invention can be applied to electronic endoscope apparatus of: the built-in color filter type which employs an imaging means including color filters (or of the type which employs an externally attached photographic camera or television camera). The following is a description of an embodiment suitable for use in applying the invention to such an electronic endoscope apparatus.

Figure 18:
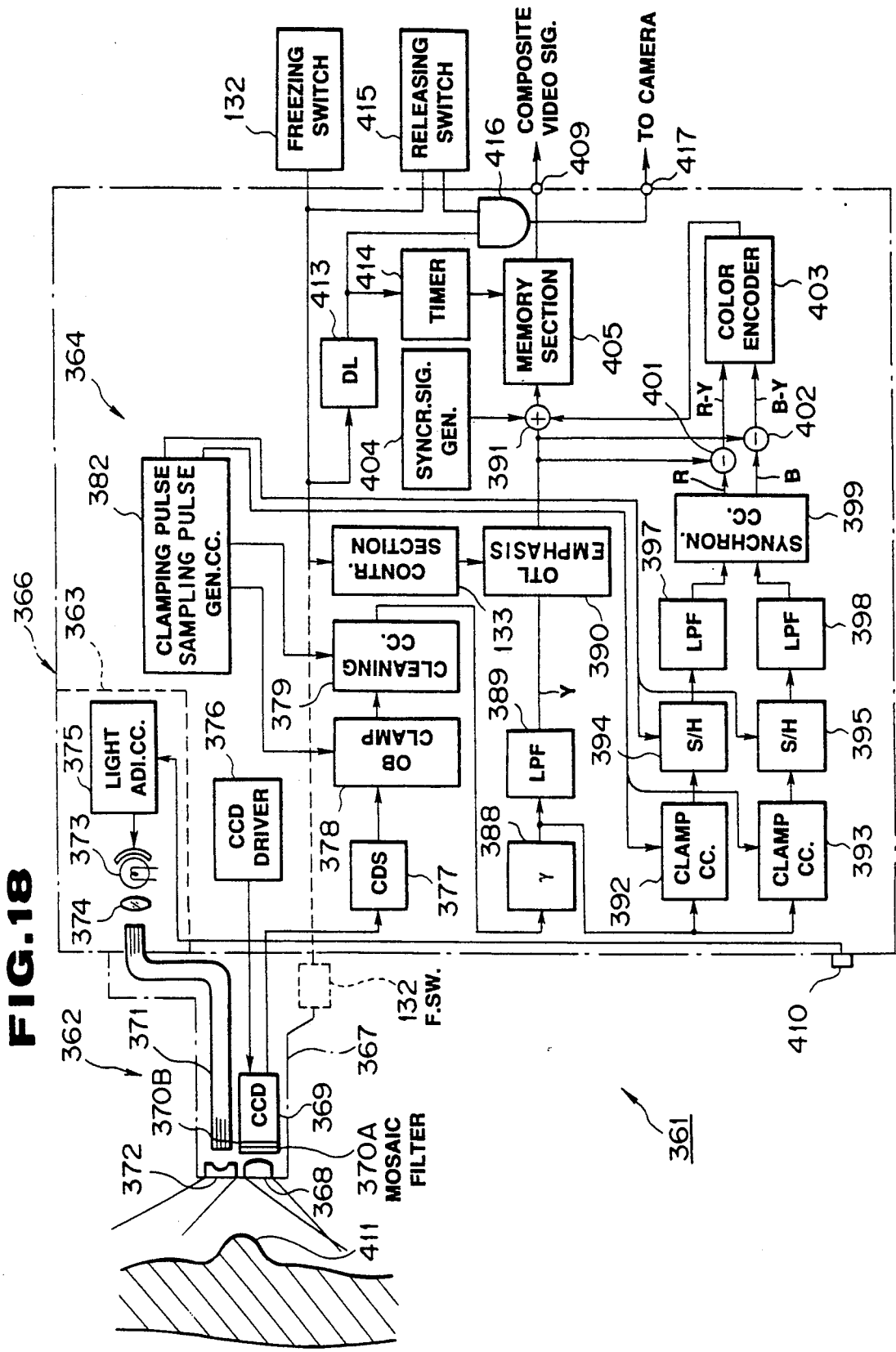
FIG. 18 is a block diagram showing an electronic endoscope apparatus according to a sixth embodiment of the present invention.

FIG. 18 shows an electronic endoscope apparatus 361 according to a sixth embodiment of the present invention.

In this embodiment, the present invention is applied to an imaging means including color filters. (This imaging means is referred to as the "simultaneous system" since video signals for one color frame can simultaneously obtained through imaging for one frame.)

The endoscope apparatus 361 is constituted by an electronic endoscope incorporating an imaging means, a light source section 363 for supplying illuminating light to the electronic endoscope 362, a video processor 366 which accommodates a signal processing section 364 for converting the signals obtained by imaging by the electronic endoscope 362 into video signals which can be displayed on a display device, and a color monitor (not shown).

The electronic endoscope 362 is provided with an elongated inserting section 367 which can be easily inserted into the body cavity, and an objective lens 368 and a CCD 369 are disposed in the front end portion of the inserting section 367, thereby forming an imaging means. A color mosaic filter 370A in which three filters which transmit red (R) light, green (G) light and blue (B) light, respectively, are disposed in a mosaic form is bonded to the imaging surface of the CCD 369.

A light guide 371 for transfer of illuminating light is transferred is inserted through the inserting section 367. The illuminating light supplied from the light source section 363 is transferred through the light guide 371 and emitted from the front end surface of the light guide 371. The emitted light passes through a projection lens 372 and illuminates an object.

The end surface of the light guide 371 which is adjacent to an operating section (not shown) can be connected to the light source section 363 for supplying illuminating light. The light source section 363 is provided with a light source lamp 373 and a condenser lens 374 for converging the white light emitted from the light source lamp 373. The quantity of light of the light source lamp 373 can be adjusted by a light adjustment circuit 375.

The objected which is illuminated by the aforesaid illuminating light is focused on the imaging surface of the CCD 336 by the objective lens 368 and is then separated into individual color components by the color mosaic filter 370A. An optical low-pass filter (LPF) 370B is provided on the imaging surface of the CCD 369 in order to prevent color moire which is primarily derived from the interference of the color mosaic filter 370A in the spatial frequency of an image of the object.

When a drive pulse for transfer and readout is applied from a CCD drive circuit 376 to the CCD 369, the object image focused on the CCD 369 is read therefrom as a photoelectrically converted signal.

The output signal of the CCD 369 is input to a correlative double sampling circuit (hereafter referred to as the "CDS circuit") 377 which constitutes a part of the signal processing section 364. The CDS circuit 377 samples and holds the feedthrough component and signal component of the output signal of the CCD 369 to extract the difference therebetween, thereby eliminating noise of 1/f or the like which primarily occurs in the CCD 369. Thus, a base-band video signal is obtained.

The output signal of the CDS circuit 377 is input to an optical black clamping circuit (hereafter referred to as the "OB clamping circuit") 378, and thus an optical black period (hereinafter referred to as the "OB period") which is the black reference level of the output of the CCD 369 is clamped at a predetermined DC level by a clamping pulse generated by a clamping pulse/sampling pulse generating circuit 382 in order to prevent a black level from fluctuating due to an increase or decrease in a dark current occurring in the CCD 369. The output signal of the OB clamping circuit 378 is input to a cleaning circuit 379 to clean the OB period and a horizontal blanking period. The output of the cleaning circuit 379 is input to a γ compensation circuit 388. The γ compensation circuit 388 serves to convert the γ characteristic of γ=1 of the output video signal of the CCD 369 into a γ characteristic of γ=0.45. The output of the γ compensation circuit 388 is input to a low-pass filter (LPF) 389, where the color signal carrier components are eliminated and thus a luminance signal Y is extracted. The luminance signal Y is input to a mixer 391 through an outline emphasis circuit 390.

In the meantime, at the front side of the low-pass filter 389, the color signal components which have been modulated in a line-sequential manner and each of which is combined with the luminance signal Y are input to clamping circuits 392 and 393. The DC levels of these input signals are fixed by the respective clamping circuits 392 and 393, and the peaks of carrier components which are modulated at the timings of the respective lines are sampled and held in corresponding sample and hold circuits 392 and 395. The outputs of the sample and hold circuits 392 and 395 are input to corresponding low-pass filters (LPFs) 397 and 398, thereby producing the base-band component of the color signal.

The thus-obtained signals, which are line-sequential color signals R and B, are respectively converted into synchronized color signals R and B by a synchronizing circuit 399 provided with a delay element having a delay time equivalent to one horizontal line, for example, a CCD type 1H delay circuit. Arithmetic circuits 401 and 402 respectively obtain the difference between the luminance signal Y and the obtained color signal R and that between the luminance signal Y and the obtained color signal G, respectively to convert the color signal R and the color signal G into corresponding color-difference signals R-Y and B-Y. The color-difference signals R-Y and B-Y are input to a color encoder circuit 403, where a single chrominance signal (hereinafter referred to as the "chroma signal") C is produced by right-angle two-phase modulation using a subcarrier.

The chroma signal C is input to the mixer 391, mixed with the luminance signal Y, and converted into a composite video signal. In addition, the mixer 391 is supplied with a composite synchronizing signal by a synchronizing signal generator 404, and the composite synchronizing signal is also added to the luminance signal Y and the chroma signal C.

The output of the mixer 391 is input to a memory section 405.

Figure 19:
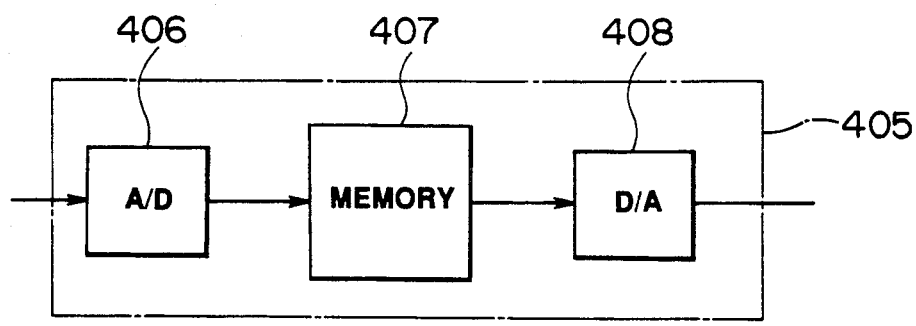
FIG. 19 is a block diagram showing the construction of a memory section according to the sixth embodiment.

As shown in FIG. 19, the memory section 405 is constituted by an A/D converter 406, a memory 407 into which digital signal data obtained by A/D conversion in the A/D converter 406, and a D/A converter 408 for converting the digital signal data read from the memory 407 into an analog signal.

The output signal of the memory section 405 is output to the color monitor (not shown) through a signal output terminal 409.

It is to be noted that this embodiment is provided with a switch 410 used to increase the quantity of illuminating light. When the switch 410 is switched on, the quantity of light emitted from the lamp 373 is increased by the light adjustment circuit 375 (a circuit capable of increasing the quantity of light) so that the quantity of light illuminating a portion 411 to be observed can be increased.

As in each of the other embodiments described above, the aforesaid outline emphasis circuit 390 is arranged such that the amount of outline emphasis thereof may be changed under the control of the control section 133 by switching on the freezing switch 132.

When the freezing signal of the freezing switch 132 is input to the control section 133, the control section 13 outputs to the outline emphasis circuit 390 a signal for changing the amount of outline emphasis and, to the memory section 405, a signal for inhibiting writing to the memory section 405 (or memory 407). More specifically, the signal which has been delayed by one frame period or one field period by the delay element 413 is input to the timer 414 and, on the basis of the output of the timer 414, writing to the memory section 405 (or memory 407) is inhibited for the period equivalent to, for example, several frames/fields to some tens of frames/fields. In consequence, the memory section 405 holds a frozen image whose outline is emphasized by an amount appropriate for the emphasis of a frozen image. If freezing operation is not carried out, the amount of outline emphasis is set to an amount appropriate for emphasis of a moving image.

When the freezing switch 132 is switched on by operating a releasing switch 415, the freezing switch 132 outputs a freezing signal to the control section 133 and the delay element 413. The signal passed through the delay element 413 is further passed through an AND gate 416 which opens in response to a gate open signal which goes high by the releasing operation, and supplied as a releasing signal through a releasing-signal output terminal 417 to a camera (used for photographing the image displayed on the color monitor) or an imaging or recording apparatus for recording still images. The releasing switch 415 may be of a type which can be switched on and off, for example, by the interlocked operation of two switches.

As shown by a dashed line in FIG. 18, the freezing switch 132 may be provided on the electronic endoscope 362 (for example, an operating section thereof).

The above-described outline emphasis circuit 390 my be constituted by either the vertical outline emphasis circuit 134 shown in FIG. 2 or the horizontal outline emphasis circuit 136-1 shown in FIG. 6 or, alternatively, a combination of the circuits 134 and 136-1 which are connected in series. Further, the outline emphasis circuit 390 may be arranged to effect horizontal and vertical outline emphases or multiple outline emphasis as shown in FIGS. 10a to 10c.

Furthermore, as the vertical outline emphasis circuit 172 shown in FIG. 12, the outline emphasis circuit 390 may be arranged to change the frequency band of an image to be processed in accordance with whether a real-time (moving) image or a frozen image is to be displayed on the monitor.

In addition, the above-described sixth embodiment may be combined with the function of changing the characteristic of the core-ring, changing the γ characteristic or displaying parent and child screens as shown in FIG. 13, 15 or 17a to 17c.

The sixth embodiment adopts a simultaneous system to which the arrangement of the frame-sequential system described above is applied. It is therefore possible to achieve effects and advantages similar to those of the frame-sequential system.

Figure 20:
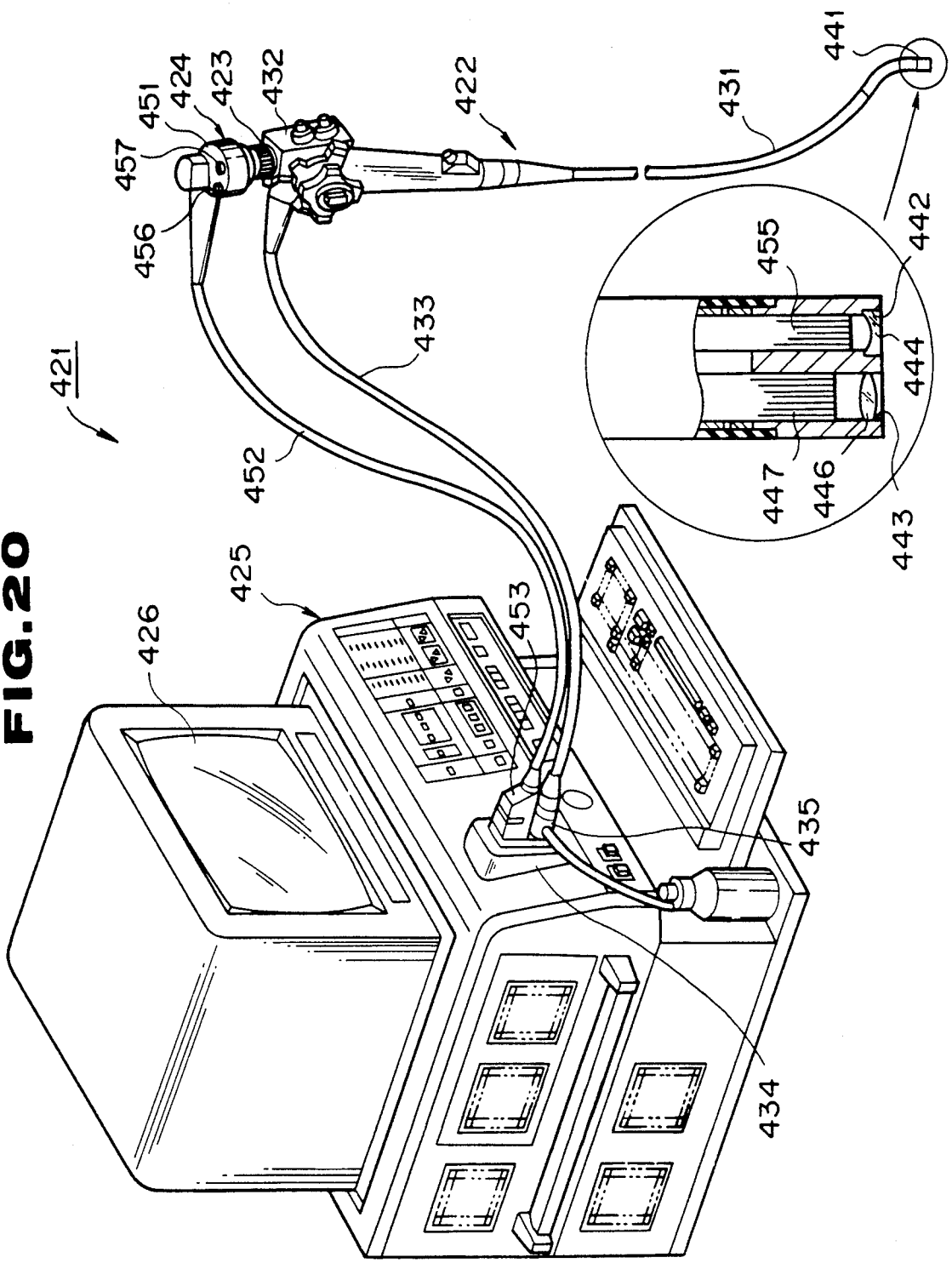
FIG. 20 is a perspective view showing the overall configuration of an electronic endoscope apparatus according to a seventh embodiment.

FIG. 20 shows an electronic endoscope apparatus 412 according to a seventh embodiment of the present invention.

The electronic endoscope apparatus 412 shown in FIG. 20 is provided with a fiber scope 422, an externally attached television camera 424 which is detachably attached to an eyepiece portion 423 of the fiber scope 422, a video processor 425 arranged to supply illuminating light to the fiber scope 422 and to effect the signal processing required for the externally attached television camera 424, and a monitor 426 arranged to receive a video signal from the video processor 425 and to provide a display of an image of an object.

The fiber scope 422 has an elongated inserting section 431 having, for example, a flexible structure, and a large diameter operating section 432 which is operated by, for example, a hand of an operator is connected to the rear end of the inserting section 431. The eyepiece portion 423 is provided at the rear end of the operating section 432. A flexible light guide cable 433 extends from one side of the operating section 432, and a light guide connector 435 which is removably connected to a connector receptacle 434 of the video processor 425 is provided at the rear end of the light guide cable 433.

An illumination window 442 and an observation window 443 are provided in an end portion 441 of the inserting section 431. A projection lens 444 is fitted in the illumination window 442, and the exit end surface of the light guide 445 is disposed at the rear side of the projection lens 444. The light guide 445 is inserted through the inserting section 431, the operating section 432 and the light guide cable 433, and the other end of the light guide 445 is connected to the light guide connector 435. The light emitted from a lamp provided in the video processor 425 is incident upon the light guide 445, passing through the exit end surface of the light guide 445 and the projection lens 444, and illuminating an object.

An objective lens 446 is disposed in the observation window 443, and the entrance end surface of an image guide 447 is disposed in the focal plane of the objective lens 446. The image guide 447 is inserted through the inserting section 431, and the exit end surface of the image guide 447 opposes an eyepiece lens 448 in the eyepiece portion 423 as shown in FIG. 19. An image of the object which is focused by the objective lens 446 is transferred to the eyepiece portion 423 through the image guide 447 so that the image can be observed through the eyepiece portion 423.

The externally attached television camera 424 is provided with a camera body 451 attached to the eyepiece portion 423, an electricity transmission cord 452 extending from the camera body 451, and a connector 453 provided at the extending end of the electricity transmission cord 452 and removably connected to the connector receptacle 434 of the video processor 425.

Figure 21:
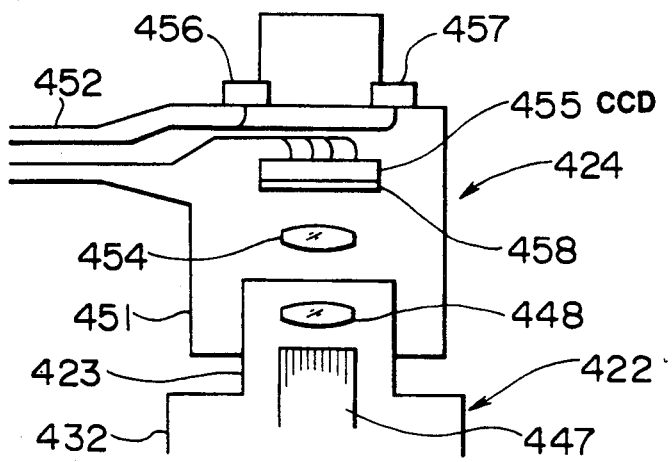
FIG. 21 is a block diagram showing the construction of a television camera according to the seventh embodiment.

As shown in FIG. 21, the camera body 451 includes a focusing lens 454 for receiving light from the eyepiece portion 423 and effecting focusing of an image of the object and a solid state imaging device or CCD 445 disposed in the focal plane of the focusing lens 454. The camera body 451 is provided with a freezing switch 456 and a releasing switch 457. A color mosaic filter 458 is attached to the imaging surface of the CCD 455 to effect color separation of received light.

The video processor 425 may be constructed by the light source section 363 and the signal processing section 364 which are shown in FIG. 18. If the color mosaic filter 458 is not attached to the imaging surface of the CCD 455 included in the television camera 424, the light source device 22 and the video processor 12 which are used in the first embodiment may be employed.

Figure 22:
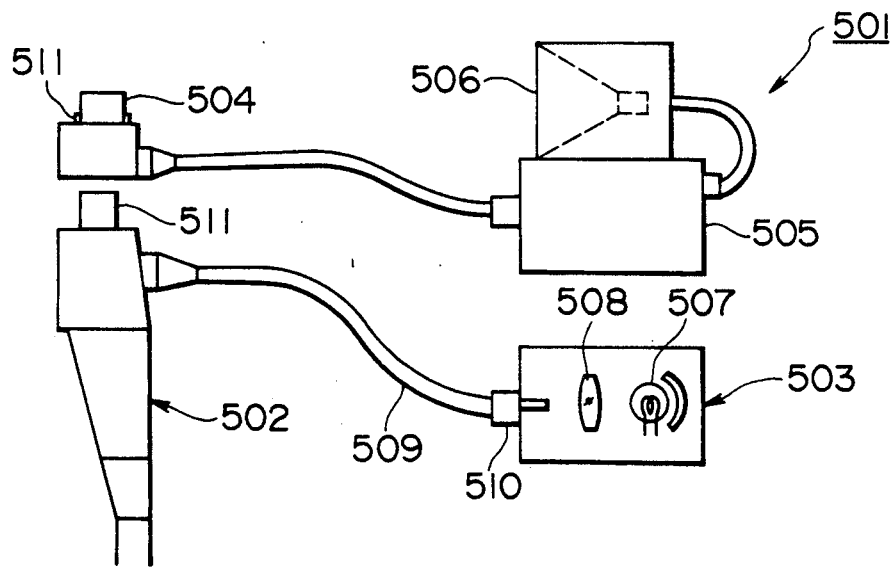
FIG. 22 is a schematic block diagram showing an electronic endoscope according to an eighth embodiment of the present invention.

FIG. 22 shows an electronic endoscope apparatus 501 according to an eighth embodiment of the present invention.

This embodiment comprises an optical endoscope apparatus including a fiber scope 502 and a light source device 503 for supplying illuminating light to the fiber scope 502, a television camera 504 which is detachably attached to the fiber scope 502, a signal processing device 505 for effecting signal processing for the television camera 504, and a color monitor 506 arranged to receive a video signal from the signal processing device 505 and display an endoscopic image on the monitor screen. Accordingly, the eighth embodiment is capable of providing a color display of an optical image obtained by the fiber scope 502.

Provision of the apparatus 501 will meet a demand for a system which can display an endoscopic image on a monitor screen by utilizing existing optical endoscope apparatus.

The construction of the fiber scope 502 may be identical to that of the fiber scope 422 shown in FIG. 20. The light source device 503 is constituted by a white lamp 507 and a condenser lens 503, and white light is supplied to a light guide connector 510 of a light guide cable 509.

The fiber scope 502 and the television camera 504 connected to an eyepiece portion 511 may have constructions identical to those of the corresponding ones shown in FIG. 21. The signal processing device 505 may be of a type which has the signal processing section 364 shown in FIG. 18. It will be understood that the amount of outline emphasis which differs from the amount of emphasis of a moving image can be selected by switching on the freezing switch 511.

The merit of the eighth embodiment is that the existing fiber scope 502 and light source device 503 can be utilized as they are.

It is apparent that further embodiments can be constructed by combining any of the above-described embodiments with a part or the whole of another embodiment.

It will be appreciated from the foregoing that, in accordance with the present invention, a means capable of changing image-quality determination factors in accordance with a real-time (moving) image and a frozen (still) image is provided, the means being switched over in accordance with whether the real-time (motion) image and the frozen (still) image is to be displayed. Accordingly, since image processing can be effected on the basis of the visual characteristics of each image to be displayed, an image appropriate for diagnosis, examination and so forth can be obtained.

What is claimed is:

1. An electronic endoscope apparatus comprising:
   (a) an electronic endoscope including
      an elongated inserting section,
      an objective optical system disposed at a front end of said inserting section for projecting and focusing illuminating light, and
      an imaging device for photoelectrically converting an optical image obtained by said objective optical system;
   (b) drive signal generating means for outputting a drive signal for causing an image signal to be read from said imaging device;
   (c) signal processing means for producing a standard video signal from the image signal read from said imaging device by applying said drive signal;
   (d) display means for providing a display of said standard video signal;
   (e) memory means for temporarily storing said video signal, said memory means constituting a part of said signal processing means;
   (f) a freezing switch for stopping input of said video signal into said memory means and for causing said memory means to repetitively output an identical still image signal;
   (g) outline emphasis means for emphasizing an outline of at least one signal read from said memory means; and
   (h) outline emphasis characteristic switching means for outputting a switching signal to change outline emphasis characteristics of said outline emphasis means in synchronization with the operation of said freezing switch.

2. An apparatus according to claim 1, wherein said outline emphasis means is constituted by a horizontal outline emphasis circuit for emphasizing a horizontal outline.

3. An apparatus according to claim 1, wherein said outline emphasis means is constituted by a vertical outline emphasis circuit for emphasizing a vertical outline.

4. An apparatus according to claim 1, wherein said outline emphasis means is a horizontal and vertical outline emphasis circuit for emphasizing horizontal and vertical outlines.

5. An apparatus according to claim 4, wherein said outline emphasis means is a multiple outline emphasis circuit for emphasizing an oblique outline in addition to horizontal and vertical outlines.

6. An apparatus according to claim 3 or 4, wherein said outline emphasis means has means for changing a band of emphasis frequencies, said mean being arranged to broaden the band of emphasis frequencies in a vertical direction when said freezing switch is switched on as compared with when said freezing switch is off.

7. An apparatus according to claim 6, wherein said means for changing the band of emphasis frequencies is constituted by two low-pass filters each having a different cutoff frequency and means for effecting switching thereof.

8. An apparatus according to claim 2 or 4, wherein said outline emphasis means is arranged to set a horizontal emphasis frequency to a high frequency when said freezing switch is switched on as compared with when said freezing switch is off.

9. An apparatus according to claim 1, wherein said outline emphasis means is arranged to increase the amount of emphasis when said freezing switch is switched on.

10. An apparatus according to claim 1, wherein said electronic endoscope is an electronic scope in which said imaging device is disposed in a focal plane of said objective optical system.

11. An apparatus according to claim 10, wherein said freezing switch is provided on said electronic scope.

12. An apparatus according to claim 1, wherein said electronic endoscope is a scope of a type to which a television camera can be externally attached, said scope including a fiber scope having an image guide an entrance end surface of which is disposed in a focal plane of said objective optical system and a television camera which is detachably attached to an eyepiece portion of said fiber scope and which includes a focusing optical system for effecting focusing of an optical image transferred through said image guide and said imaging device for photoelectrically converting said optical image focused by said focusing optical system.

13. An apparatus according to claim 10 or 12, wherein said imaging device is of a type in which a color filter for effecting color separation is disposed at a front of the imaging surface of said imaging device.

14. An apparatus according to claim 10 or 12, wherein said imaging device is of a type in which no color filter for effecting color separation is disposed at a front of the imaging surface of said imaging device.

15. An apparatus according to claim 10 or 12, wherein said light emitting means has a light guide which is arranged to transfer illuminating light supplied to an entrance end surface from an external light source device and then to emit said illuminating light through an exit end surface.

16. An apparatus according to claim 12, wherein said freezing switch is provided on said television camera.

17. An apparatus according to claim 1, wherein said outline emphasis characteristics change an emphasis quantity.

18. An apparatus according to claim 1, wherein said outline emphasis characteristics change an emphasis frequency.

19. An electronic endoscope apparatus comprising:
   (a) an electronic endoscope including
      an elongated inserting section,
      an objective optical system disposed at a front end of said inserting section for projecting and focusing illuminating light, and
      an imaging device for photoelectrically converting an optical image obtained by said objective optical system;

(b) drive signal generating means for outputting a drive signal for causing an image signal to be read from said imaging device;
(c) signal processing means for producing a standard video signal from the image signal read from said imaging device by applying said drive signal;
(d) display means for providing a display of said standard video signal;
(e) memory means for temporarily storing said video signal, said memory means constituting a part of said signal processing means;
(f) a freezing switch for stopping input of said video signal into said memory means and for causing said memory means to repetitively output an identical still image signal;
(g) low-level part suppressing means for suppressing a low-level part of an outline emphasis signal for at least one signal to be read from said memory means; and
(h) switching means for switching a suppressing quantity of said low level part suppressing means in synchronization with operation of said freezing switch.

20. An apparatus according to claim 19, wherein said low-level signal suppressing means is arranged to suppress a low-level input signal over a wide range when said freezing switch is on as compared with when said freezing switch is off.

* * * * *

UNITED STATES PATENT AND TRADEMARK OFFICE
CERTIFICATE OF CORRECTION

PATENT NO.   :   5,034,888

DATED        :   July 23, 1991

INVENTOR(S)  :   Masao UEHARA et al

It is certified that error appears in the above-identified patent and that said Letters Patent is hereby corrected as shown below:

On the cover page, Item [75], line 3, after "Kanno", insert -- Katsuyoshi Sasagawa; Shinji Yamashita; Jun Hasegawa,--.

Signed and Sealed this

Twenty-seventh Day of April, 1993

Attest:

MICHAEL K. KIRK

Attesting Officer

Acting Commissioner of Patents and Trademarks